United States Patent [19]
Frenier

[11] Patent Number: 6,118,000
[45] Date of Patent: Sep. 12, 2000

[54] METHODS FOR PREPARING QUATERNARY AMMONIUM SALTS

[75] Inventor: Wayne W. Frenier, Katy, Tex.

[73] Assignee: Hydrochem Industrial Services, Inc., Houston, Tex.

[21] Appl. No.: 09/250,854

[22] Filed: Feb. 17, 1999

Related U.S. Application Data

[62] Division of application No. 08/742,290, Nov. 4, 1996, abandoned.

[51] Int. Cl.$^7$ ............... C07D 215/00; C07D 211/92; C07D 213/18; C07D 213/20
[52] U.S. Cl. ............................ 546/152; 546/347
[58] Field of Search ..................... 546/347, 152

[56] References Cited

U.S. PATENT DOCUMENTS

| | | | |
|---|---|---|---|
| Re. 30,714 | 8/1981 | Harriman et al. | 134/2 |
| Re. 30,796 | 11/1981 | Lesinski | 134/2 |
| 3,404,094 | 10/1968 | Keeney et al. | 252/148 |
| 3,413,160 | 11/1968 | Teumac | 148/6.14 |
| 4,071,746 | 1/1978 | Quinlan | 252/392 |
| 4,539,140 | 9/1985 | Quinlan | 252/390 |
| 4,637,899 | 1/1987 | Kennedy, Jr. | 252/82 |
| 4,734,259 | 3/1988 | Frenier et al. | 252/8.555 |
| 5,096,618 | 3/1992 | Frenier | 252/396 |

FOREIGN PATENT DOCUMENTS

WO/94/04645  3/1994  WIPO.

OTHER PUBLICATIONS

Chemical Abstracts 123:313968, Bymaster, 1995.
Chemical Abstracts 66:72278, Law, 1967.
Casreact 123:228348, Miura, 1995.
Casreact 107:198156, Hosomi, 1987.
Casreact 106:196234, Ezquerra, 1986.
Casreact 106:4823, Alvarez–Builla, 1986.
Casreact 102:131885. Yamaguchi, 1985.

*Primary Examiner*—D. Margaret Seaman
*Attorney, Agent, or Firm*—Shook, Hardy & Bacon LLP

[57] ABSTRACT

The present invention is directed to methods for preparing quaternary ammonium salts, particularly pyridinium and quinolinium salts. By preparing these salts in a solvent selected from the group consisting of propylene glycols, propylene glycol ethers and mixtures thereof, the production of undesirable by-products and contamination of the product with undesirable solvents are minimized, if not eliminated. Using the preparation methods of the present invention low hazard corrosion inhibitors and aqueous cleaning solutions using these inhibitors may be prepared. In fact, by preparing dodecyl pyridinium bromide in dipropylene glycol methyl ether as the solvent, a particularly desirable corrosion inhibitor characterized by a low toxicity and a high flash point has been prepared. The present invention thus provides the safer corrosion inhibitors and cleaning solutions long sought by industrial cleaning services.

20 Claims, 14 Drawing Sheets

DDPB Preps at 200 °F
Equimolar Amounts of Pyridine and 1-Bromododecane

Cleaning of Pen-II Tubes in 10% Sol A
300 °F, 0.25% Inhibitor

Cleaning of Pen-II Tubes in 10% Sol B
200 °F, 0.25% Inhibitor

Cleaning of Pen-II Tubes in 2% Sol D
200 °F, 0.30% Inhibitor

Cleaning of Pen-II Tubes in 3% Sol C
200 °F, 0.30% Inhibitor

Cleaning of Pen-II Tubes in 10% Sol E
150 °F, 0.25% Inhibitor

Corrosion Rate of Pen-II Tubes
After Cleaning Plateau

Removal of Copper from Steel in Sol A
150°F, 0.2% Inh., Air and Anti-foam

Removal of Copper from Steel in 10% Sol A at 150 °F
0.2% Inh., M240 Pumped at 350 mL/min Removal of Copper from Steel in 10% Sol A at 150 °F
M240, Parr Bomb at 80 RPM Removal of Copper from Steel in 10% Sol A at 150 °F
S/V = 0.6 cm$^{-1}$, M240, 0.2% Inhibitor Removal of Copper from Steel in 10% Sol A at 130 °F
S/V = 0.6 cm$^{-1}$, M240, 0.2% Inhibitor Removal of Copper from Steel in 10% Sol A at 110 °F
S/V = 0.6 cm$^{-1}$, M240, 0.2% Inhibitor Dynamic Scale Dissolution Tests in 10% Sol A
at 300 °F, 0.25% Inhibitor, Pen-II Tubes Dynamic Scale Dissolution Tests in 10% Sol B
at 200 °F, 0.25% Inhibitor, Pen-II Tubes Dynamic Scale Dissolution Tests in 3 % Sol C
at 200 °F, Pen-II Tubes Dynamic Scale Dissolution Tests in 10 % Sol E at 150 °F, Pen-II Tubes Dynamic Cleaning of Georgia Pwr. Tubes in 10% Sol A, 0.25% Inhibitor at 300 °F Copper Removal from Georgia Pwr. Tubes in 10% Sol A
0.25% Inhibitor at 150 °F Cleaning of Georgia Pwr. Tubes in Sol A
Inhibited with 0.25% 25-4-32

Cleaning of Hamilton Tubes in 10% Sol A at 300 °F with 0.25% Inhibitor

Copper Dissolution from Hamilton Tubes in 10% Sol A with M240 and 0.25% Inh. at 150 °F Parr Bomb Preps of DDPB in DPM, 50% of BDD added at 0 Hrs.,
and 50% added at 1 Hrs.

Glassware Quat Preps in 43% DPM, 212-240 °F

Production of DDPB with DPM in 200 Gal Reactor

Cleaning of B&W Boiler with ChelClean™ 675 Solvent and 0.15% Field Test Inhibitor Cleaning of B&W Boiler with ChelClean™ 675 Solvent
Copper Stage with Air/$H_2O_2$ at 150 °F Cleaning of B&W Boiler with ChelClean™ 675 Solvent
Copper Stage with Air/$H_2O_2$ at 150 °F

METHODS FOR PREPARING QUATERNARY AMMONIUM SALTS

This application is a divisional of U.S. patent application Ser. No. 08/742,290, filed Nov. 4, 1996, and abandoned at a time when it was co-pending with this application.

BACKGROUND OF THE INVENTION

1. Field of the Invention

The present invention generally relates to methods for preparing quaternary ammonium salts and low hazard corrosion inhibitors using those salts. More specifically, the present invention is directed to methods particularly useful for producing pyridinium and quinolinium salts, to low hazard corrosion inhibitors using those salts and to aqueous cleaning solutions using those inhibitors.

2. Description of the Background

Scale comprised of insoluble salts is typically found on the surface of all types of metal equipment in which water is evaporated or heat transfer occurs. These salt deposits are particularly undesirable because of their negative impact on the heat transfer efficiency of the equipment. Because the equipment loses heat transfer efficiency as these deposits build up, it is necessary to periodically clean the equipment to remove the deposits. Industrial cleaning service companies often provide the required cleaning services for this equipment, e.g., the boilers and heat transfer equipment of utilities and industrial plants.

The undesirable scales which must be removed generally comprise calcium and magnesium salts deposited during the evaporation of hard water. Exemplary of these scales are deposits including calcium carbonate, calcium sulfate, calcium phosphate and calcium oxylate. While calcium and magnesium salts comprise the majority of these deposits, salts of other materials may be encountered. Scales high in iron content, e.g., scales including magnetite or hematite, often must be cleaned.

The conventional cleaning operations rely upon the circulation of aqueous cleaning solutions through the equipment, e.g., boilers, heat exchangers and associated piping in an effort to dissolve the salt deposits comprising the scale. Often, these cleaning solutions are heated to temperatures above the boiling point of water. In many early cleaning efforts highly acidic solutions were circulated through the equipment to dissolve the calcium and magnesium salts found in the hard water scale and the magnetite and hematite deposits encountered in high iron scales. As cleaning operations became more sophisticated, solutions containing agents capable of complexing the metals associated with the deposited salts were circulated in order to loosen and dissolve the scale. Ammonia has been used as an alkaline complexing agent for this purpose. See, e.g., the disclosure in U.S. Pat. No. 3,413,160. More recent developments have included complexing agents based upon ethylenediaminetetraacetic acid and related compounds.

Because many of these cleaning solutions are, themselves, corrosive to the metal components of the equipment being cleaned, the solutions must include appropriate corrosion inhibitors. For example, aliphatic pyridinium and quinolinium salts, together with sulphur-containing compounds, have been employed successfully as corrosion inhibitors in these solutions. See, e.g., the disclosure in U.S. Pat. No. 4,637,899 which is incorporated herein by reference. While these corrosion inhibitors provide the desired protection of the metal surfaces, they are often contaminated with unsafe and/or toxic byproducts, e.g., solvents and unreacted reactants, resulting from the methods by which they were prepared. Accordingly, these corrosion inhibitors and cleaning solutions produced therefrom can present dangers to the employees working with them. Another danger associated with the use of these corrosion inhibitors is the low flash point, often less than 100° F., resulting from the solvents and resistants which were used in their manufacture. Still another danger may result from the toxicity of its sulfur-containing compounds employed in these corrosion inhibitors. For example, ethylene glycol monobutyl ether is a toxic chemical used as a solvent and carried along with the aliphatic pyridinium salts used in the methods and corrosion inhibitors disclosed in the '899 patent. Thiourea is an undesirable sulfur-containing compound typically used in these inhibitors and methods.

As environmental and worker safety concerns have increased, the need to employ less toxic corrosion inhibitors and cleaning solutions has increased. Further, as OSHA requirements and worker safety issues have evolved, the benefits of employing corrosion inhibitors and cleaning solutions with higher flash points has become clear. The industrial cleaning service industry has continued to seek improved corrosion inhibitors and cleaning solutions for use in commercial, scale cleaning operations. The known methods and solutions have not solved these problems. Thus, there has been a long felt but unfulfilled need in the industrial cleaning service industry for less toxic and safer corrosion inhibitors and cleaning solutions. The present invention solves those needs.

SUMMARY OF THE INVENTION

The present invention is directed to methods for preparing quaternary ammonium salts and particularly pyridinium and quinolinium salts. These methods are particularly useful in preparing low hazard corrosion inhibitors characterized by low toxicity and high flash points. These low hazard corrosion inhibitors are particularly useful in aqueous cleaning solutions for safely and effectively removing scale deposits from the interior of boilers and heat exchangers.

In the methods of the present invention a quaternary ammonium salt is prepared by contacting a tertiary ammonium compound with a second compound having the formula RX where R is aliphatic, substituted aliphatic or alkyl aryl and X is an anion. Preferably R is selected from the group consisting of alkyl and alkyl aryl moieties having from about 6 to about 18 carbon atoms and X is a halide, most preferably chloride or bromide. The foregoing compounds are reacted in a solvent selected from the group consisting of propylene glycols, propylene glycol ethers and mixtures thereof, most preferably dipropylene glycol methyl ether. The reaction is conducted at a temperature greater than about 65° C., preferably in the range of about 75° C. to about 125° C. Optionally, the reaction may proceed in the presence of water. In its most preferred embodiment, the present invention comprises a method for preparing dodecyl pyridinium bromide by contacting pyridine with dodecyl bromide in dipropylene glycol methyl ether at a temperature above about 65° C.

The foregoing methods of the present invention produce mixtures of reaction product and solvent characterized by lower toxicity than mixtures prepared by conventional methods for preparing similar quaternary ammonium salts. Accordingly, salts prepared in accord with the present invention may be used to prepare improved, low hazard corrosion inhibitors. Not only do such corrosion inhibitors exhibit lower toxicity, but they also are characterized by high flash points than are similar inhibitor compositions prepared by prior methods. These improved corrosion inhibitors may be used to prepare safer aqueous cleaning solutions.

A low hazard composition useful for inhibiting corrosion of steel contacted by organic acids, chelating agents or sulfuric acid may comprise the reaction product of the foregoing methods, a sulfur-containing compound and a nonionic surfactant. These corrosion-inhibiting compositions may be prepared in the solvent in which the reaction product was prepared, in water or in a mixture of both. Particularly useful corrosion inhibitors may comprise 20–50 percent-by-weight of a mixture of the quaternary ammonium compound prepared by the foregoing methods of the present invention and the solvent used in preparing that compound, about 1–10 percent-by-weight of a sulfur-containing compound and about 0–10 percent-by-weight of a nonionic surfactant. The balance of the corrosion inhibitor composition may comprise water, the solvent or mixtures thereof. Not only are these corrosion inhibitors less toxic, but they are safer to handle, typically having flash points at least about 140° F. Such corrosion inhibitors are characterized by both lower toxicity and high flash point than similar compositions prepared by prior methods. These improved qualities may be attributed to the use of propylene glycol and propylene glycol ether as reaction solvents.

In a final aspect of the present invention, improved aqueous cleaning solutions employing the quaternary ammonium salts produced by the foregoing methods are disclosed. Typical of these solutions are aqueous cleaning solutions having a pH from about 1–10 and comprising at least one organic acid selected from the group consisting of alkylene polyamine polyacetic acids, hydroxyacetic acids, citric acid and mixtures or salts thereof, together with an effective amount of a corrosion inhibitor including quaternary ammonium salt prepared in accord with the methods of the present invention. In another aspect of the present invention, aqueous cleaning solutions comprising at least one acid selected from the group consisting of sulfuric acid, hydrochloric acid and phosphoric acid, together with an effective amount of a corrosion inhibitor including a quaternary ammonium salt produced by the methods of the present invention, are disclosed. The cleaning solutions of the present invention are safer than those produced using prior methods.

The present invention provides methods for producing quaternary ammonium salts useful in applications where reduced hazard levels, e.g., low toxicity, are required. The present invention provides methods for producing improved corrosion inhibitors characterized by lower toxicity and higher flash points. Accordingly, these corrosion inhibitors provide health and safety benefits to the industrial cleaning industry where they may be used to formulate industrial cleaning solutions.

Thus, the long felt but unfulfilled need in the industrial cleaning industry for safer corrosion inhibitors and aqueous cleaning solutions has been met. These and other meritorious features and advantages of the present invention will be more fully appreciated from the following detailed description and claims.

BRIEF DESCRIPTION OF THE DRAWINGS

Other features and intended advantages of the present invention will be more readily apparent by the references to the following detailed description in connection with the accompanying drawings, wherein.

Figure 1:
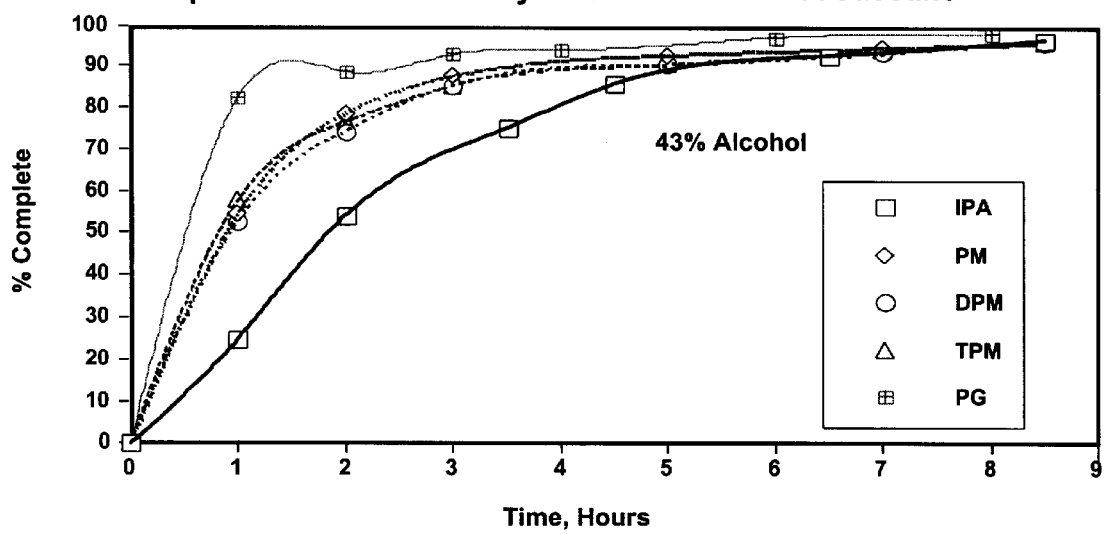
FIGS. 1 to 28 are graphical representations of test data, e.g., reaction coordinates and corrosion tests, for the claimed methods for preparing quaternary ammonium salts and for corrosion inhibitors using these salts.

While the invention will be described with reference to the presently preferred embodiments, it will be understood that it is not intended to limit the invention to those embodiments. On the contrary, it is intended to cover all alternatives, modifications and equivalents as may be included in the spirit of the invention as defined in the appended claims.

DETAILED DESCRIPTION OF THE PREFERRED EMBODIMENTS

The present invention is directed in its broadest sense to methods for preparing quaternary ammonium salts by contacting a tertiary ammonium compound with a second compound having the formula RX where R is aliphatic, substituted aliphatic or alkyl aryl and X is an anion. In the present invention the contacting proceeds in a solvent selected from the group consisting of the propylene glycols, propylene glycol ethers and mixtures thereof. In the most preferred method, pyridine is contacted with dodecyl bromide in dipropylene glycol methyl ether (DPM) to produce dodecyl pyridinium bromide (DDPB) and mixtures thereof in DPM.

Quaternary ammonium salts prepared in accord with the present invention and mixtures of those salts in the solvent of preparation are characterized by a lower toxicity and higher flash point than similar salts and mixtures prepared by methods using conventional solvents, e.g., isopropanol (IPA), ethylene glycol and ethylene glycol monobutyl ether (EB). The methods of the present invention are particularly useful for producing quaternary ammonium salts, most particularly DDPB, for use in applications requiring lower toxicity and higher flash points. While there are applications for those products in cosmetics, toiletries and other personal hygiene products, DDPB and mixtures thereof with DPM have been found particularly useful in the preparation of improved corrosion inhibitors and aqueous cleaning solutions including those inhibitors.

A conventional corrosion inhibitor and aqueous cleaning solutions using that inhibitor were disclosed in U.S. Pat. No. 4,637,899. While the cleaning solutions described therein have been quite successful, those in the industrial cleaning service would welcome cleaning solutions having lower toxicity and higher flash points. A preferred cleaning solution prepared in accord with the disclosure of the '899 patent and using conventionally prepared DDPB is characterized by a low flash point (88° F.) and includes isopropanol and two components, thiourea and EB, both considered toxic. Lethal dose toxicity values for thiourea and EB, respectively, are only 125 mg/kg and 1500 mg/kg for $LD_{50}$ (oral rats). Thiourea also has been listed on the registers of the National Toxicity Program and the International Agency for Research on Cancer as a possible cancer causing agent in animals. Isopropanol used both in the preparation of DDPB and as a solubilizing alcohol is relatively toxic, with as little as 100 ml being fatal to humans. Accordingly, it would be desirable to replace these components with less toxic components without adversely affecting the corrosion-inhibiting characteristics of the composition.

It was well known that propylene glycol and propylene glycol ethers have much lower toxicities than ethylene glycol and corresponding ethylene glycol ethers. The propylene glycols and propylene glycol ethers also have relatively high flash points, e.g., greater than 150° F. However, it was not clear that quaternary ammonium salts, and in particular DDPB, could be synthesized in propylene glycol or propylene glycol ethers, a necessary step in eliminating isopropanol as a reaction solvent and component of the finished corrosion inhibitors.

Propylene glycol and its ethers are generally characterized by higher flash points than the solvents used in the prior methods. For example, the flash points of propylene glycol (PG) and dipropylene glycol methyl ether (DPM), respectively, are 210° F. and 175° F. More importantly, propylene glycol and its ethers are significantly less toxic than isopropanol or ethylene glycol monobutyl ether. For example, the lethal dose toxicity values, $LD_{50}$ (oral rats), for PG and DPM are very high at 20,000 mg/kg and 5130 mg/kg, respectively. Thus, propylene glycol and its ethers would not only produce compositions with higher flash points but, more significantly, compositions with markedly lower toxicity.

In the methods of the present invention, a quaternary ammonium salt is prepared by contacting a tertiary ammonium compound with a second compound having the formula RX where R is aliphatic, substituted aliphatic or alkyl aryl and X is an anion. The choice of anion is not critical and may be varied for convenience. Examples of suitable anions include chloride, bromide, iodide, nitrate, methyl sulfate, bisulfate, tosylate, acetate, benzoate, dihydrogen phosphate and the like. Bromide and chloride are the preferred anions.

In a more preferred embodiment, the tertiary ammonium compound is selected from the group consisting of aromatic ammonium compounds, more preferably, pyridine, alkyl pyridine, quinoline, alkyl quinoline and mixtures thereof. Even more preferably, the tertiary ammonium compound may be represented by the formula

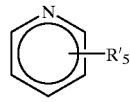

wherein each $R'_5$ independently is —H, —OH, —OR, —OROH, alkyl, alkenyl, alkynyl or halo. In the more preferred embodiment, the second compound having the formula RX is selected from the alkyl halides and the alkyl aryl halides having from about 6 to about 18 carbon atoms. More preferably, this second compound is selected from the benzyl halides, naphthyl halides and alkyl halides having from about 7 to about 16 carbon atoms.

In the most preferred embodiments, the tertiary ammonium compound is pyridine, quinoline or a mixture thereof while the second compound is an alkyl bromide, an alkyl aryl chloride or a mixture thereof. Most preferably, the tertiary ammonium compound is pyridine while the second compound is dodecyl bromide.

In the present invention, the contacting proceeds in a solvent selected from the group consisting of propylene glycol, propylene glycol ethers and mixtures thereof. While propylene glycol may be used, the propylene glycol ethers are preferred. More preferred are the propylene glycol aliphatic and aromatic ethers, particularly those wherein the aliphatic substituent has from 1 to 4 carbon atoms or the aromatic substituent is phenyl. Exemplary propylene glycol ethers include propylene glycol methyl ether, dipropylene glycol methyl ether, tripropylene glycol methyl ether, propylene glycol phenyl ether, propylene glycol methyl ether acetate and dipropylene glycol monomethyl ether acetate.

Water may optionally be added as an additional solvent during the contacting step. The importance of the solvent in quaternization reactions is well known. These reactions usually proceed more quickly in polar solvents than in nonpolar solvents due to the formation of ions as the reactions proceed. While polar molecules, e.g., the glycol ethers and water, are excellent solvents, there are several problems with these chemicals. If separation of the quaternary salt is desired, the polar solvents can be difficult to remove from the products. While the presence of water accelerates the reaction, water may also react with the alkyl bromide to form an alcohol and hydrogen bromide, thus reducing the yield of the reaction. Thus, caution must be taken with respect to the addition of water.

The preparation of the quaternary ammonium salts is conducted at a temperature greater than about 65° C., preferably from about 75° C. to about 125° C. In the presently most preferred embodiment, pyridine and dodecyl bromide are contacted in dipropylene glycol methyl ether at about 110° C. to about 115° C.

Quaternary ammonium salts prepared by the foregoing methods may be used as components of low hazard corrosion inhibitor compositions useful for inhibiting the corrosion of steel contacted by organic acids, inorganic acids and chelating agents. Generally, these corrosion-inhibiting compositions will include about 20–50 percent-by-weight of a mixture of the quaternary ammonium salt and solvent prepared in accord with the foregoing procedures by reacting a tertiary ammonium compound with a second compound having the formula RX where R is aliphatic, substituted aliphatic or alkyl aryl and X is an anion and the solvent is selected from the group consisting of the propylene glycols, propylene glycol ethers and mixtures thereof. The tertiary ammonium compound and second compound RX are preferably added in about equal molar ratios. The weight ratio of quaternary ammonium salt to solvent in the final reaction mixture, while preferably about 1.5 to 1, may be in the range of about 0.5 to 1 to about 2.0 to 1.

These corrosion inhibitor compositions include about 1–10 percent-by-weight of a sulphur-containing compound, preferably a compound where sulfur is in the −2 oxidation state. The sulfur-containing compound is also selected for its low toxicity. The sulfur-containing compound enhances the corrosion-inhibiting protection afforded by the quaternary ammonium salt component of the corrosion inhibitor. The sulfur-containing compound is employed in an amount that is sufficient to improve the protection afforded by the quaternary ammonium salt. Typically, improved protection is achieved by including at least about 0.2 moles of the sulfur-containing compound per mole of the quaternary ammonium salt. The corrosion inhibitor composition of the present invention preferably includes from about 0.2 to about 2 moles of sulfur-containing compound per mole of quaternary ammonium salt. Exemplary sulphur compounds include the thiocyanate salts, mercaptoacetic acid and its salts, diethyl thiourea, dibutyl thiourea, diethyl dithio carbamic acid, its salts and methyl derivatives, trithio carbamic salts and mixtures thereof. Most preferably, the sulphur-containing compound is mercaptoacetic acid, diethyl thiourea or ammonium thiocyanate and mixtures thereof.

It is desirable, but not necessary, to employ a surfactant in the corrosion inhibitor compositions of the present invention. An individual surfactant or a mixture of several surfactants may be used. Exemplary nonionic surfactants include ethoxylated nonyl phenols, alkyl aryl polyether alcohols, aliphatic polyether alcohols, alcohol ethoxy sulfates and alkyl sulfonated diphenyl oxides. The most preferred surfactant is ethoxylated nonyl phenol (with 15 EO). When used, the surfactant is employed in an amount that aids the rate of dispersion or dissolution of the corrosion inhibitor composition into a concentrated cleaning solution. The surfactant preferably is employed in an amount that is from about 0–10 percent-by-weight, and more preferably from about 3–7 percent-by-weight based on the final corrosion inhibitor composition.

The balance of these corrosion inhibitor compositions is comprised of a solubilizing alcohol, preferably the propylene glycol or propylene glycol methyl ether solvent used in preparation of the quaternary ammonium salt, water and mixtures thereof. Known solubilizing alcohols include the alkanols, alkenols, alkynols, glycols, polyols and mixtures thereof. While any of these conventional solubilizing alcohols may be employed, in order to achieve the low hazard characteristics of the present invention, the solubilizing alcohol should be chosen from the propylene glycols, propylene glycol ethers and mixtures thereof. The alcohols improve the solubility of the components in the inhibited cleaning solutions and also improve the handling properties of the final compositions. Examples of these properties include freezing point and rate of dispersion or dissolution into the cleaning solution. A preferred embodiment of the present invention is a corrosion inhibitor composition containing at least one alcohol or its ether in an amount sufficient to prevent the corrosion inhibitor composition from freezing under conditions of storage and use. Preferred solubilizing alcohols include propylene glycol and dipropylene glycol methyl ether.

Corrosion inhibitors in accord with the foregoing composition are characterized by high flash points, i.e., flash points typically above about 140° F., and reduced toxicity when compared to previously used compositions.

The foregoing corrosion inhibitor compositions are particularly useful as components of aqueous cleaning solutions to retard and minimize the corrosion of metal parts, particularly steel, being cleaned with these solutions. For the purpose of the present invention, the term "cleaning solution" refers to an aqueous acidic or alkaline solution that is employed in the cleaning of metal surfaces, e.g., the internal metal surfaces of process equipment. These cleaning solutions typical have a pH in the range of about 1 to about 10. Exemplary cleaning solutions and their uses are disclosed in several patents, e.g., U.S. Pat. Nos. 3,413,160; 4,637,899; Re.30,796; and Re.30,714, all of which are incorporated herein by reference.

Cleaning solution compositions in accord with the present invention may include at least one organic acid selected from the group consisting of alkylene polyamine polycarboxylic acids, hydroxyacetic acid, formic acid, citric acid and mixtures or salts thereof together with a corrosion inhibitor in accord with the foregoing compositions present in an amount effective to inhibit the corrosion of metals in contact with the solution. Exemplary organic acids include EDTA, tetraammonium EDTA, diammonium EDTA, HEDTA and salts thereof. These aqueous cleaning solutions typically exhibit a pH from about 1 to about 10. Exemplary amounts of corrosion inhibitor are from about 0.05 to about 1 percent-by-weight wherein the quaternary ammonium salt is present in an amount from about 5 to about 50 percent-by-weight of the inhibitor. Exemplary organic acid cleaning solutions and typical pHs are shown in Table 1.

TABLE 1

Typical Organic Acid Cleaning Solutions

| Active Agent(s) | pH |
| --- | --- |
| HEDTA[1] | 2.3 |
| diammonium EDTA[2] | 5 |
| tetraamonium EDTA[2] | 9.2 |
| tetraamonium EDTA and citric acid | 5 |
| tetraamonium EDTA and formic acid | 5 |
| hydroxyacetic and formic acids | 2.2 |
| trisodium salt of B + $H_2SO_4$ | 1.2–1.5 |

[1]HEDTA is N-2-hydroxyethyl N,N',N'-ethylene diamine triacetic acid.
[2]EDTA is N,N,N',N'-ethylene diamine tetracetic acid.

The corrosion inhibitor compositions of the present invention may also be used in aqueous cleaning solutions to inhibit the corrosion of metal by a variety of inorganic acids, e.g., sulfuric acid, hydrochloric acid and phosphoric acid. These cleaning solutions include an amount of corrosion inhibitor in accord with the present invention that is sufficient to inhibit the corrosion of metals by these inorganic acids. Exemplary amounts of corrosion inhibitor are from about 0.05 to about 1 percent-by-weight wherein the quaternary ammonium salt is present in an amount from about 5 to about 50 percent-by-weight of the inhibitor.

Corrosion inhibitors in accord with the present invention prevent, or at least minimize, excess corrosion of clean base metal during chemical cleaning operations. The corrosion inhibitor compositions may be employed advantageously over a wide pH range in a wide number of cleaning solutions employing an organic acid as the cleaning agent.

Cleaning solutions are employed predominantly in the removal of scale and rust from ferrous metals. However, the solutions often contact other metals that are present as an integral part of the system being cleaned. Examples of those metals include copper, copper alloys, zinc, zinc alloys and the like.

The corrosion inhibitor compositions of the present invention advantageously are employed in an amount sufficient to inhibit acid-induced corrosion of metals that are in contact or contacted with aqueous cleaning solutions. Typically, the corrosion inhibitor compositions of the present invention are employed in an amount sufficient to give a corrosion rate less than or equal to about 0.015 lb/ft$^2$/day. Preferably, from about 145–2900 mg/l of corrosion inhibitor, measured as the sum of the quaternary ammonium salt and the sulfur-containing compound, are employed in the cleaning solution, based on the total volume of the final inhibited cleaning solution. Preferably, the amount of the quaternary ammonium salt employed ranges from about 120–2400 mg/l, and the amount of sulfur-containing compound that is employed ranges from about 25–500 mg/l. The amount of corrosion inhibitor composition employed is dependent upon the composition of the specific cleaning solution to be inhibited. For example, the presence of hydroxy ethyl ethylene diamine triacetic acid requires a relatively large amount of corrosion inhibitor composition. Preferably, the corrosion inhibitor composition is dissolved or dispersed in the cleaning solution prior to contacting the cleaning solution and the metal to be cleaned.

The following examples and comparative examples are merely illustrative of the present invention. These examples should not be construed as limiting in scope. All parts and percentages are by weight unless otherwise specified.

Preparation of Dodecyl Pyridinium Bromide

Dodecyl pyridinium bromide (DDPB) was prepared in a stirred three neck flask (250 ml) fitted with a reflux condenser and a type j thermocouple probe. Heat was supplied by a Glascol mantel controlled with an IR$^2$ digital temperature controller. In each test, 64.2 grams of alcohol, glycol or glycol ether, 20.7 grams of pyridine (0.26 mole) and 65.1 grams (0.26 mole) of 1-bromo dodecane were placed in the flask. The flask was heated with stirring to 85° C. An exotherm was encountered which caused the temperature to rise to about 100° C. The temperature controller was adjusted to 95° C. and this temperature was maintained throughout the preparation. At set times, samples were drawn and the bromide concentration was determined on a Mettler Model 25 autotitrator using the chloride specific ion silver nitrate method. The reaction was terminated when the bromide concentration reached 96% of the theoretical value.

Where dipropylene glycol methyl ether (DPM) and tripropylene glycol methyl ether (TPM) were used as solvents, it was necessary to add 10 ml of water at the six-hour time mark to drive the reaction to completion. The concentration of DDPB in isopropyl alcohol, propylene glycol and propylene glycol methyl ether was 57 percent-by-weight while the concentration in DPM and TPM was 54 percent-by-weight FIG. 1 illustrates the rates and percent completion of these preparations. All of the preparations reached at least 95% completion in about eight hours at 95° C. The comparative preparation in isopropyl alcohol took the longest to reach completion. The three preparations in glycol ethers were essentially equivalent, while the preparation in propylene glycol was the fastest of the five reactions. It must be noted that the preparations in DPM and TPM required the addition of water to force the reaction to proceed to greater than 95% completion.

Because of the exothermic nature of the reaction, it may be necessary to add the second compound, 1-bromo dodecane, slowly or incrementally during the reaction process.

Cleaning Solutions

Cleaning solutions inhibited with corrosion inhibitors prepared in accord with the present invention were prepared, tested and compared with a conventional corrosion inhibitor (A251) prepared in accord with the disclosure in the '899 patent. Corrosion inhibitors were prepared for use with the following organic acid cleaning solutions:

TABLE 2

| Cleaning Solutions | |
|---|---|
| Cleaning Solution | Active Agent(s) |
| 10% Sol A | 4% tetraammonium EDTA |
| 10% Sol B | 4% diammonium EDTA |
| 3% Sol C | 3% hydroxyacetic acid and formic acid |
| 2% Sol D | 2% formic acid and citric acid |
| 10% Sol E | 4% trisodium HEDTA (sulfuric acid to pH 1.4) |

Test Specimens

Carbon steel specimens (1018 CS) were purchased from Corrosion Test Supplies, Inc. of French Settlement, La.

Rings for conducting scale solution tests were obtained from Pennsylvania Electric Co. The boiler from which the tubes were removed was a Combustion Engineering combined circulation boiler. From the chemical analysis the tubes were determined to be SA-213-T22 alloy steel (2.25% Cr). These tubes are later referenced as the Pen-II tubes.

Carbon steel tube sections from Georgia Power Co. at Milledgeville, Ga., having scale containing both magnetite and copper were obtained for other tests.

Finally, carbon steel tubes from the city of Hamilton, Ohio, were also tested. These tubes included a heavy scale deposit having 37% iron and 24% copper deposited at the rate of 20 g/ft$^2$.

Static Corrosion Tests

Static corrosion tests were conducted using conventional pressure bombs. For each test, a single 1018 CS coupon having a surface area of 36.22 cm$^2$ was weighed and placed in the glass bomb liner with 90 ml of solvent (s/v=0.4 cm$^{-1}$) inhibited with 0.1% of the test formulation. The liner also contained a Teflon cylinder to reduce the solvent volume. The bombs were closed and placed in an oil bath that had been raised to the test temperature. After 24 hours at the test temperature the test coupons were removed, cleaned and re-weighed.

Iron Oxide Scale Dissolution Tests

Iron oxide scale dissolution was determined from the following procedure. Rings were cut from the Pen-II tubes and machined to a constant surface area of 50 cm$^2$. For each test, three of the rings were placed in 250 ml of inhibited solvent in a stirred titanium Parr bomb for 24 hours at the test temperature. Samples were periodically removed and the iron concentration determined using a Perkin-Elmer inductively coupled plasma spectrometer. It was presumed that the cleaning plateau indicated that the surfaces were cleaned. A corrosion rate for the time period following the plateau was calculated from the change in iron concentration between the plateau and the end of the tests.

Copper Removal Tests

The removal of iron oxide and copper from utility power boilers is often accomplished using a two step procedure employing tetraammonium EDTA. Iron oxide is dissolved under reducing conditions at a temperature up to about 300° F. The temperature is then lowered to about 150° F. and an oxidant, e.g., oxygen, air or hydrogen peroxide, introduced to oxidize ferrous EDTA to ferric EDTA. This chemical then passivates the steel and oxidizes any copper that plated onto the steel during the iron removal stage. It is critical that an inhibitor protect steel during the iron removal stage but not interfere with passivation and copper removal during the copper removal stage.

To test the effect of inhibitors prepared in accord with the present invention on copper removal, the following simulation was used. A concentrate of ferrous EDTA was produced by heating 25% Sol A cleaning solution with iron powder. Two 1018 CS coupons were heated for 24 hours at 300° F. in 400 ml of a solution containing ferrous EDTA (about 4,000 ppm iron), sufficient cupric acetate to give about 500 ppm copper, free EDTA (about 2%) and about 0.2% inhibitor. This portion of the test simulated the iron removal stage and plating of copper.

After 24 hours the solutions were sampled to determine iron and copper concentrations using the Perkin-Elmer inductively coupled plasma spectrometer and free EDTA by the copper specific ion electrode method. The pH was adjusted to 9.3 with ammonium hydroxide, the free EDTA cleaning solution adjusted to 2% and the solvent and coupons placed in the test cell. The solutions containing the copper plated coupons were heated to 150° F. Air was passed through the solutions at 700 ml/min and the pH values and EMF (Pt vs. S.C.E.) were measured for three hours. Foam was controlled by adding conventional anti-foaming agents. The solution was sampled periodically to determine iron and copper concentrations and the pH was maintained at 8.7 at 150° F., corresponding to a pH of 9.2 at 75° F. After three to four hours of exposure to the oxidizing solution, the coupons were removed and examined.

In another experiment, the ferrous EDTA was oxidized using 30% hydrogen peroxide (M240) and circulated over the copper plated coupons at 350 ml/min for a total of four hours. The pH was maintained at 8.7 in situ (corresponding to a pH of 9.2 at 75° F.) with ammonium hydroxide and the EMF maintained at greater than −100 mv (vs. S.C.E.) by periodic addition of 30% hydrogen peroxide.

In a final experiment to better quantify the effects of the inhibitor on copper removal, the steel coupons were treated with the concentrated ferrous EDTA solution described above, but modified to contain 3% free EDTA, for 24 hours at 300° F. After this exposure, the solution was cooled to 150° F. and 10 ml of 30% hydrogen peroxide introduced, along with 2 ml of ammonium hydroxide. The solution was stirred at 80 rpm for 5 hours, during which the concentrations of iron and copper were measured at various times.

Static Corrosion Rates

Static corrosion rates were determined for three inhibitor formulations prepared with dodecyl pyridinium bromide prepared in accord with the present invention and compared with the corrosion rates observed for similar inhibitors prepared using isopropyl alcohol. These formulations were prepared to contain 42% of the reaction mixture of the DDPB/solvent preparation, 5% ammonium thiocyanate, 5% nonyl phenol (15 EO) surfactant and 48% water. A concentration of 0.1% volume was used to inhibit Sol A at 300° F. and Sol B at 200° F. All of these formulations were found to be effective inhibitors of corrosion of 1018 CS coupons under the test conditions. The results are reported in Table 3.

TABLE 3

Corrosion Rates of DDPB/NH$_4$SCN Mixes for 1018 CS with 0.1% Inh.

| Alcohol in Mix | Sol A Corrosion Rate (lb/ft$^2$/day) | Sol B Corrosion Rate (lb/ft$^2$/day) |
| --- | --- | --- |
| A251 | 0.0015 | 0.0035 |
| 2-Propanol | 0.0018 | 0.0032 |
| PM | 0.0014 | 0.0032 |
| DPM | 0.0018 | 0.0032 |
| TPM | 0.0014 | 0.0035 |

Formulations with a variety of concentrations of the DDPB/DPM solvent preparation, sulfur-containing compound (ammonium thiocyanate) and nonionic surfactant (nonyl phenol with 15 EO) were prepared. The corrosion rates in Sol A inhibited with 0.1% of these formulations were determined. These results are reported in Table 4 below.

TABLE 4

DDPB/DPM Mix Optimization

| DDPB/DPM (%) | Nonyl Phenol (15 EO) (%) | HN$_4$SCN (%) | Sol A Corrosion Rate (lb/ft$^2$/day) |
| --- | --- | --- | --- |
| 40.00 | 5.000 | 2.000 | 0.00140 |
| 40.00 | 2.500 | 5.000 | 0.00170 |
| 50.00 | 2.500 | 2.000 | 0.00180 |
| 30.00 | 2.500 | 2.000 | 0.00150 |
| 30.00 | 2.500 | 8.000 | 0.00140 |
| 50.00 | 2.500 | 8.000 | 0.00180 |
| 40.00 | 0.000 | 2.000 | 0.00260 |
| 40.00 | 0.000 | 8.000 | 0.00240 |
| 30.00 | 5.000 | 5.000 | 0.00120 |
| 30.00 | 0.000 | 5.000 | 0.00340 |
| 50.00 | 0.000 | 5.000 | 0.00280 |
| 40.00 | 5.000 | 8.000 | 0.00140 |
| 40.00 | 2.500 | 5.000 | 0.00130 |
| 40.00 | 2.500 | 5.000 | 0.00170 |
| 50.00 | 5.000 | 5.000 | 0.00120 |
| 45.00 | 5.000 | 5.000 | 0.00140 |
| 0.00 | 0.000 | 0.000 | 0.02400 |
| 30.00 | 2.500 | 1.000 | 0.00350 |
| 20.00 | 2.500 | 5.000 | 0.00170 |
| 20.00 | 2.500 | 2.500 | 0.00180 |

The remainder of each formulation is water

Table 4 seems to indicate that the corrosion rates are reduced not only by DDPB and ammonium thiocyanate, but also by the surfactant. This data suggests that corrosion inhibition is a complex process which may be improved by selection of the nonionic surfactant.

Additional formulations were prepared using different solvents wherein the concentration of the DDPB/solvent mixture was maintained at 40 percent. These formulations included 2% ammonium thiocyanate and 2.5 to 5% surfactant. Formulations and corrosion rates are shown in Table 5.

TABLE 5

Properties of DDPB/Alcohol or Glycol Mixes

| Formulation | DDPB/ Solvent (%) | NH$_4$SCN (%) | Water (%) | Solvent (%) | Surfactant (%) | IPA (%) | Corrosion Rate Sol A | Corrosion Rate Sol B |
| --- | --- | --- | --- | --- | --- | --- | --- | --- |
| 18-22-27 | 40 | 2 | 0 | 55, PG | 2.5 | 0 | 0.0019 | 0.0032 |
| 18-22-29 | 40 | 2 | 27.5 | 0 | 2.5 | 27.5 | 0.0019 | 0.0030 |
| 18-23-23 | 40 | 2 | 13.5 | 41.5, DPM | 2.5 | 0 | 0.0019 | 0.0018 |
| 18-23-33 | 40 | 2 | 13.5 | 39.5, DPM | 5.0 | 0 | 0.0013 | 0.0032 |

Corrosion rate is lb/ft$^2$/day.

The results of copper removal tests for these formulations are reported in Table 6.

TABLE 6

Copper Removal Data

| Inhibitor/ Anti-foaming Agent | Conc. Inh. (%) | Oxidizer | Test Condition | Time Hrs | Copper Remaining (%) |
|---|---|---|---|---|---|
| A251/M45 | 0.2 | Air | 700 ml/min | 3 | 10 |
| 18-23-33/M45 | 0.2 | Air | 700 ml/min | 3 | 80 |
| 18-23-33/ M246 | 0.2 | Air | 700 ml/min | 4 | 0 |
| A251 | 0.2 | Peroxide | Pump 350 ml/min | 4 | 20 |
| 18-23-33 | 0.2 | Peroxide | Pump 350 ml/min | 4 | 70 |
| A251 | 0.2 | Peroxide | Stirred 80 rpm | 5 | 25 |
| 18-23-33 | 0.1 | Peroxide | Stirred 80 rpm | 5 | 70 |
| 18-23-33 | 0.2 | Peroxide | Stirred 80 rpm | 5 | 80 |

Figure 2:
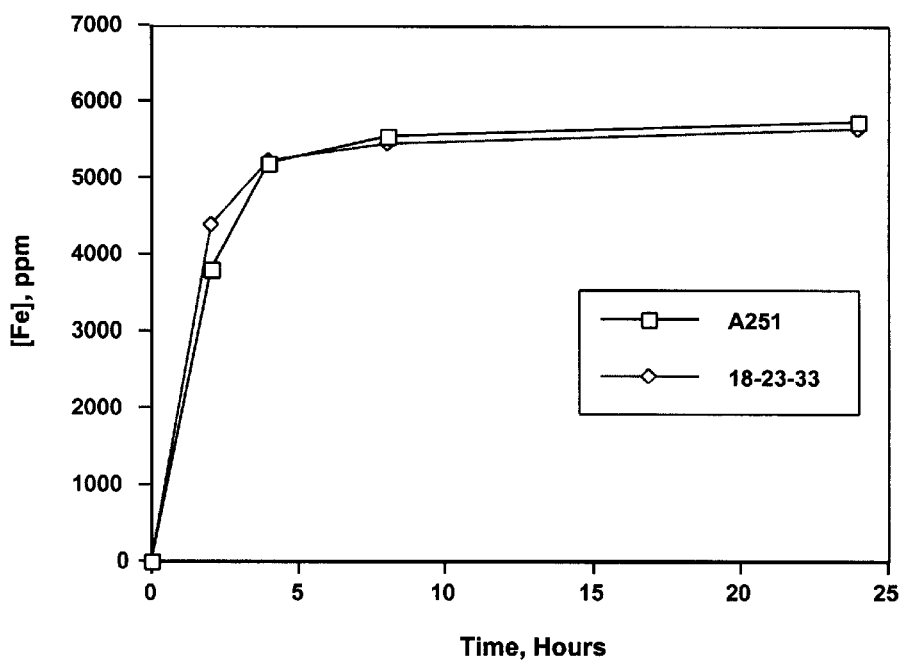
Figure 3:
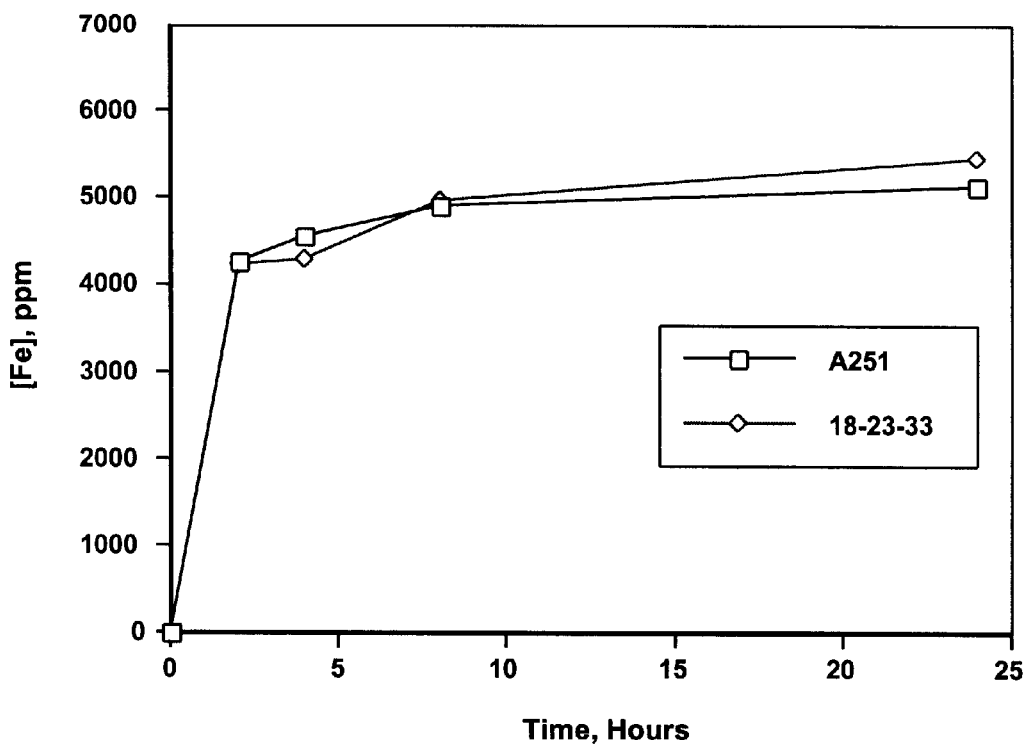
Figure 4:
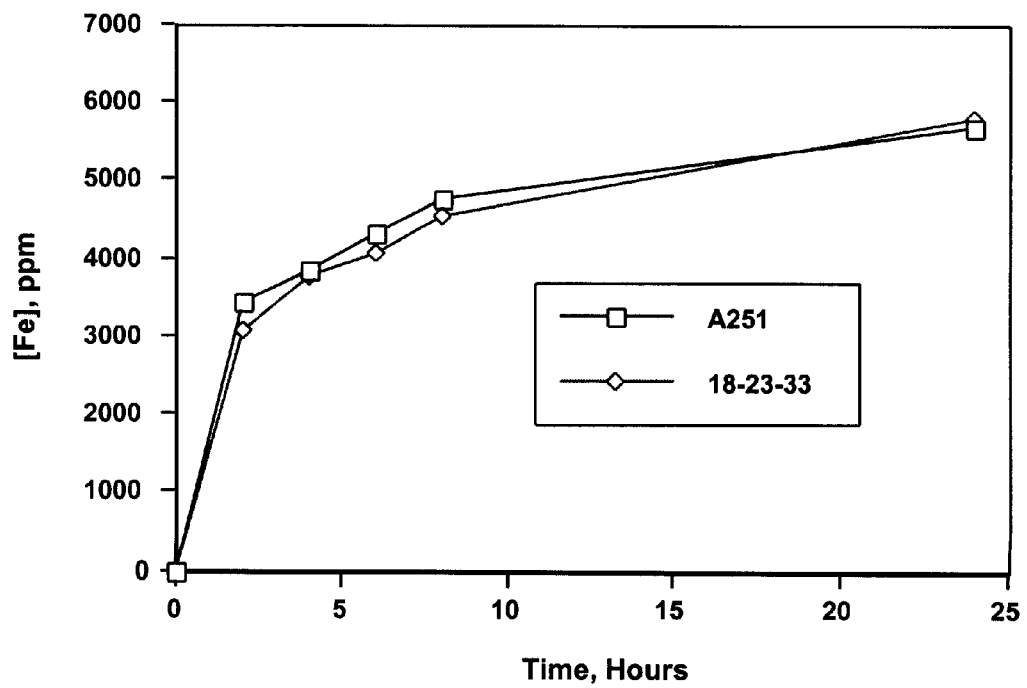
Figure 5:
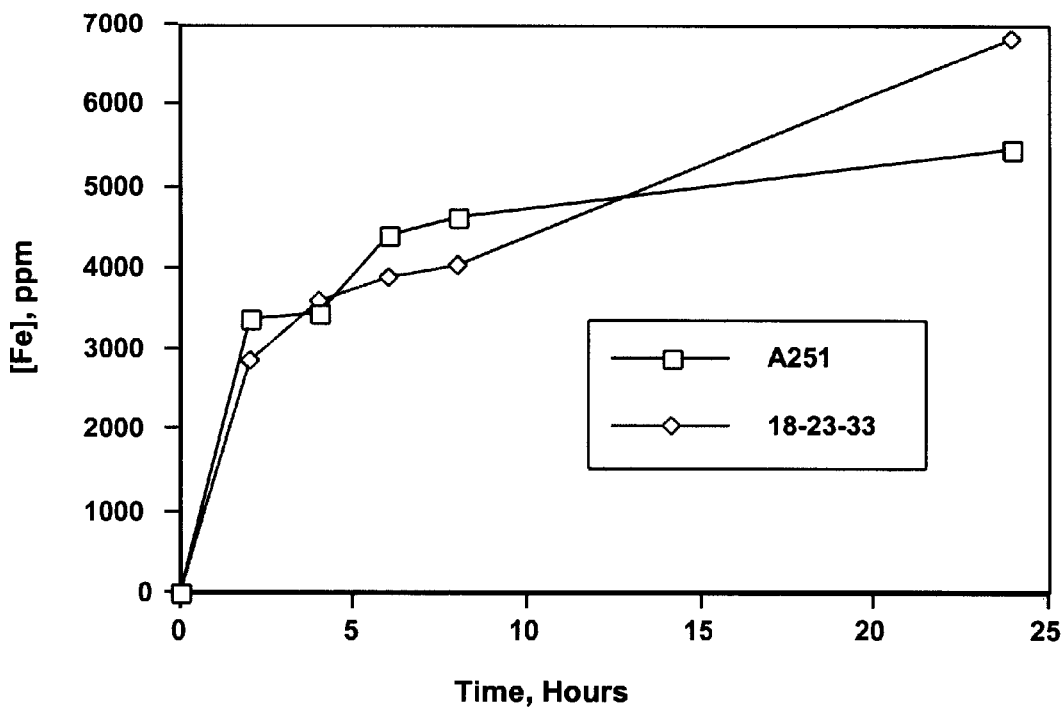
Figure 6:
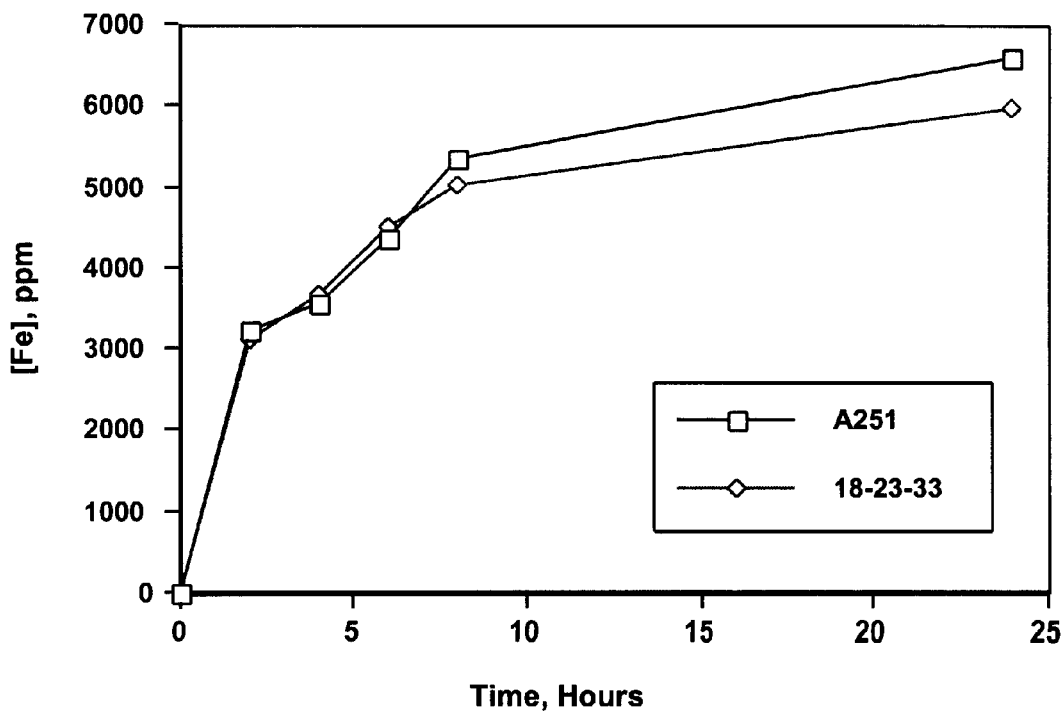

Additional tests were conducted with corrosion inhibitor 18-23-33. These included iron oxide scale dissolution tests conducted in the cleaning solutions and using the method described above. FIGS. 2–6 illustrate the results of these tests. Each figure compares the results observed with a cleaning solution including a corrosion inhibitor prepared in accord with the present invention (formulation 18-23-33) to results of a formulation prepared in accord with the '899 patent (A251). The curves in FIGS. 2–4 are virtually identical, thus establishing that the low hazard corrosion inhibitor of the present invention provides results essentially identical to the results of the more hazardous conventional inhibitors. While it would appear from FIG. 5 that the corrosion inhibit or of the present invention is not as effective as the conventional solution in Sol C cleaning solution, FIG. 6 indicates that the inhibitor of the present invention is better than the prior inhibitor when used with Sol E cleaning solutions.

Figure 7:
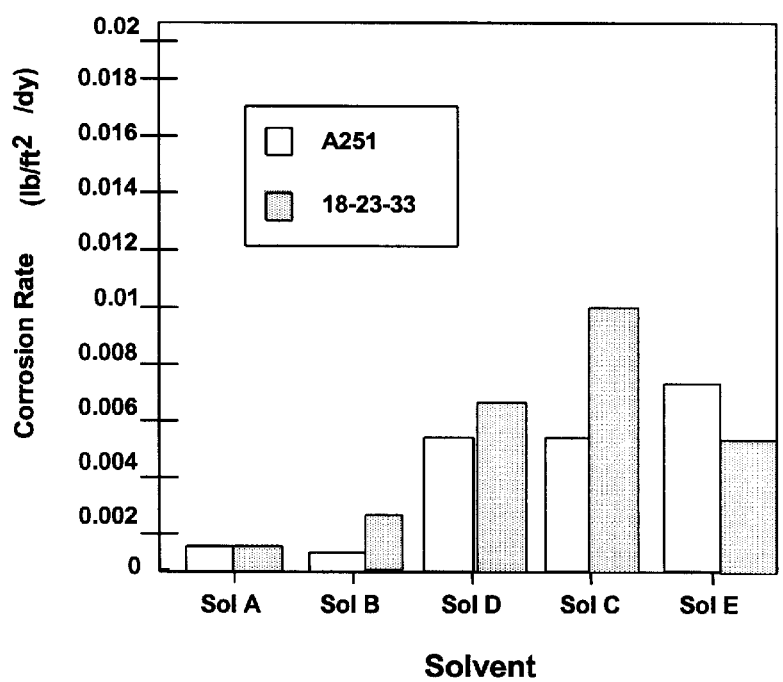

The post plateau corrosion rates for each of the cleaning solutions illustrated in FIGS. 2–6 are compared in FIG. 7. It is obvious from FIG. 7 that all of these solutions provide acceptable corrosion rates of less than 0.015 lb/ft$^2$/day.

Figure 8:
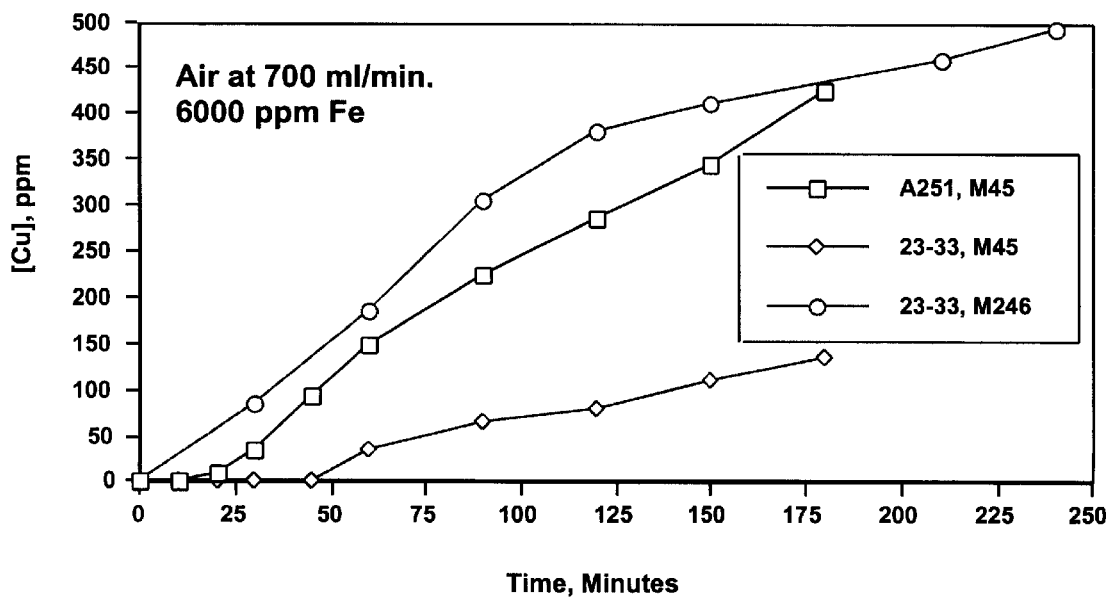
Figure 9:
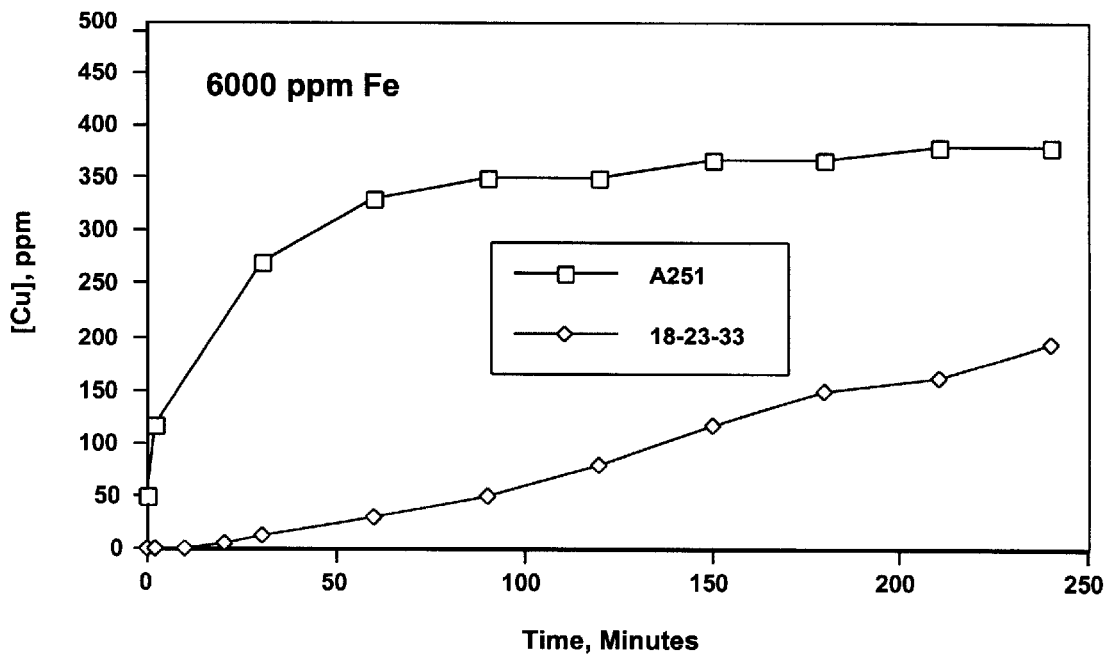
Figure 10:
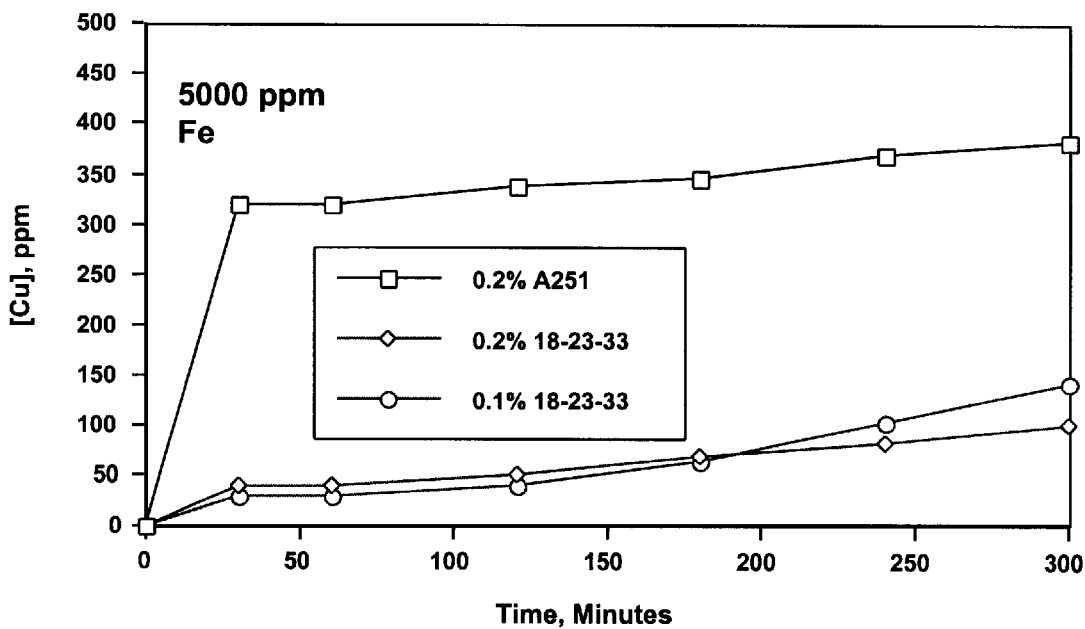

The results of copper removal tests in accord with the previously described method are illustrated in FIGS. 8–10. These tests compare the results of corrosion inhibitor 18-23-33 with the conventional A251 inhibitor. Air blow tests are illustrated in FIG. 8. The solutions initially contained 6000 ppm iron. After three hours about 80% of the copper had been removed from the solution inhibited with A251 while only about 30% of the copper had been removed from the solution inhibited with 18-23-33. Both solutions included a conventional, silicone anti-foaming agent (M45). When another conventional, alcohol anti-foaming agent (M246), was substituted in the formulation with 18-23-33, copper removal was significantly improved. About 90% removal was achieved after three hours with removal substantially complete at four hours. Because the iron concentrations remained substantially constant, it may be assumed that corrosion of the steel coupon was insignificant.

FIGS. 9 and 10 illustrate additional results using hydrogen peroxide as the oxidizer.

Additional copper removal tests were conducted in Sol A cleaning solution. A copper solvent was synthesized containing ferrous EDTA, free EDTA and enough hydrogen peroxide to oxidize all of the iron to the ferric state. The solvent contained 554 g ferrous EDTA (1.8% iron), 80 g Sol A, 1365 g water and 40 g 30% hydrogen peroxide. A weighed copper coupon having a surface area of 37.8 cm$^2$ was placed into 100 ml of this copper solvent along with a test amount of inhibitor, typically 0.2% in a stainless steel test bomb. The temperature was maintained at 160° F. for six hours, after which the copper coupon was retrieved, dried and weighed.

The effect of the inhibitor on copper removal from steel was also tested. Four 1018 CS coupons with 36 cm$^2$ surface area were heated in a stirred Parr bomb for 24 hours at 350° F. in a solution containing ferrous EDTA (4000 ppm iron), sufficient cupric acetate to give about 500 ppm copper, free EDTA and 0.2% inhibitor. The solution was prepared from the following components: 55 ml ferrous EDTA (1.8% iron), 100 ml 10% Sol A, 0.34 g cupric acetate, 100 ml water and 0.5 ml inhibitor (0.2%). This part of the test was designed to simulate the iron removal stage and the plating of copper. After 24 hours the solutions were cooled to the test temperature and sampled to determine iron and copper concentration. An additional 2 ml of the Sol A and 6% ml of 30% hydrogen peroxide were injected and the solution stirred at 80 rpm for the duration of the test. The tests were sampled periodically to determine the concentrations of iron and copper. At the end of the tests the coupons were examined for the presence of residual iron and the solvent was filtered through a 0.45 micron filter.

Tests to determine the ability to remove copper were conducted on several corrosion inhibitor formulations using a variety of sulfur-containing compounds.

TABLE 7

Corrosion Inhibitor Formulations with Different Sulfur Compounds

| Formulation | DDPB (%) | DPM (%) | Surfactant (%) | Water (%) | Sulfur (%) | Compound |
|---|---|---|---|---|---|---|
| 20-16-35 | 21 | 52 | 4.5 | 17.5 | 5 | diethyl thiourea |
| 20-28-12 | 21 | 50 | 5 | 17 | 5 | diethyl thiourea |
|  |  |  |  |  | 2 | ammonium thiocyanate |
| 20-48-23 | 20 | 52 | 5 | 16 | 5 | mercaptoacetic acid |
| 20-65-4 | 21 | 16 | 5 | 38 | 20 | 25% Na$_2$CS$_3$ |

Figure 11:
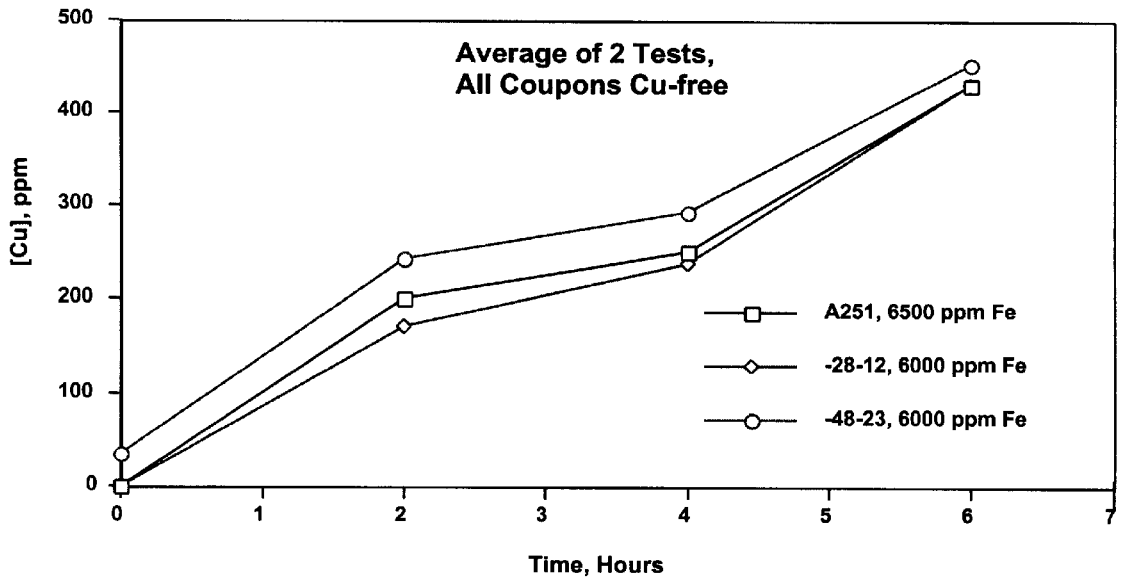
Figure 12:
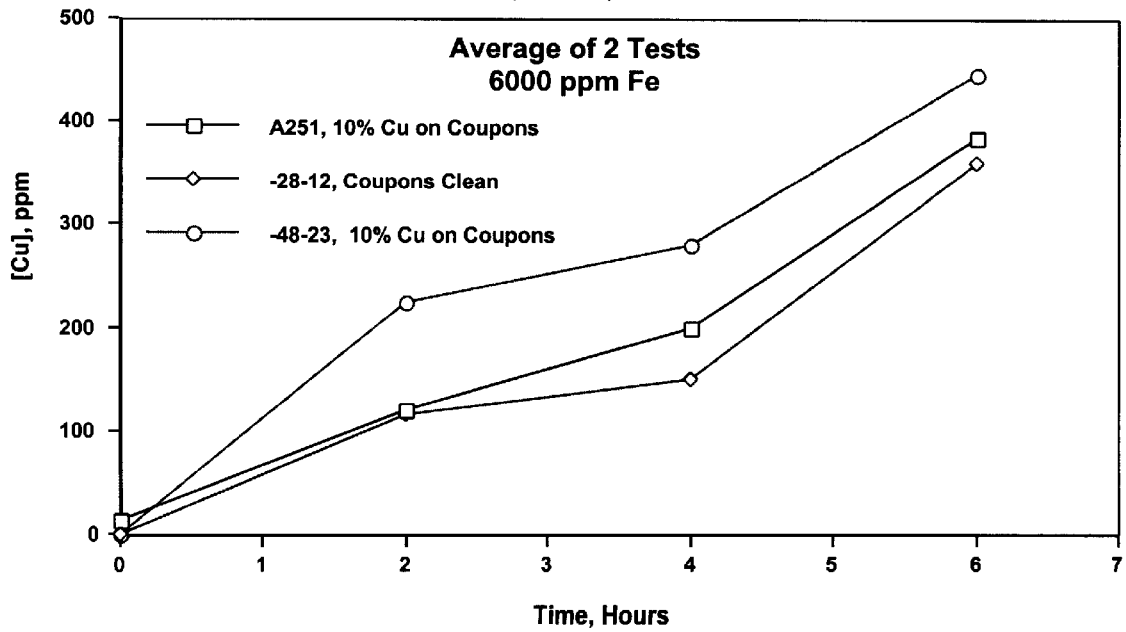
Figure 13:
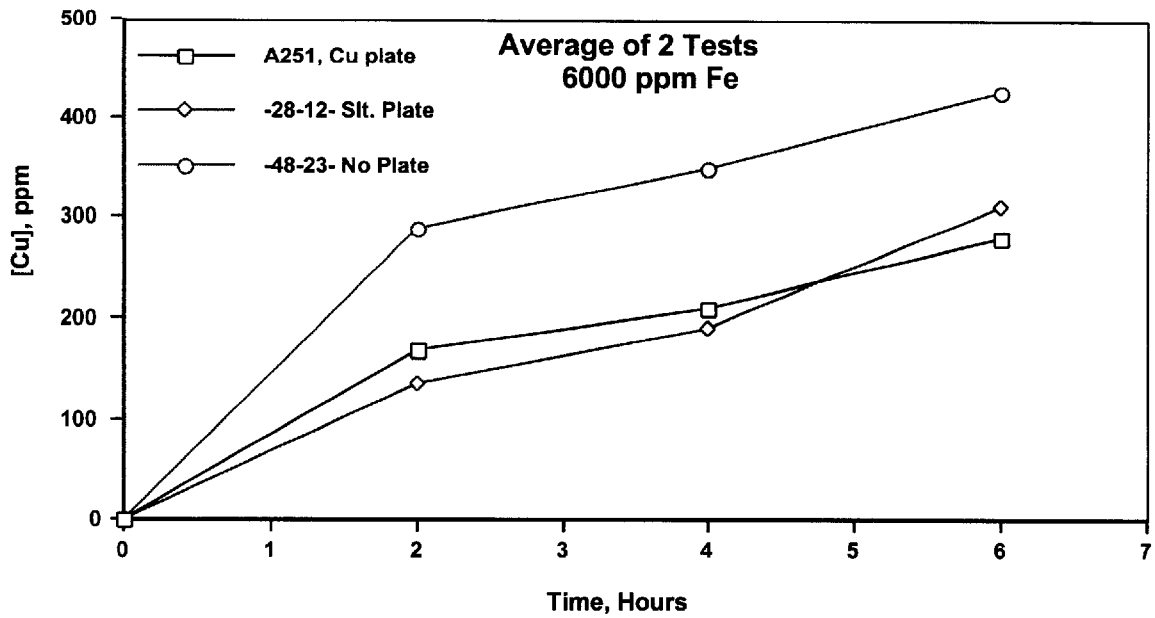
Figure 14:
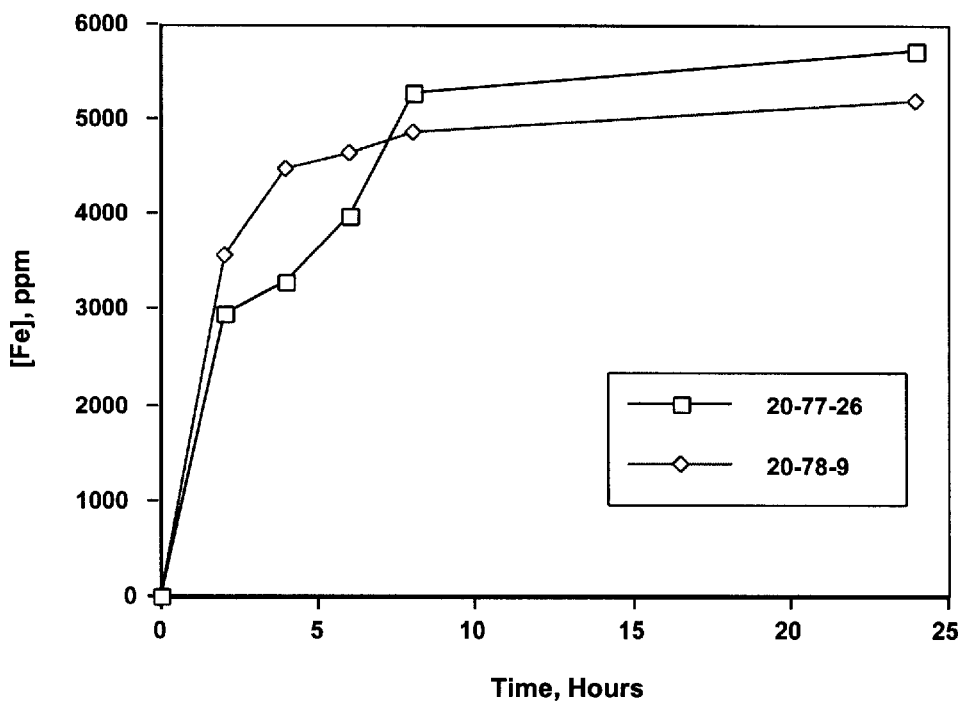
Figure 15:
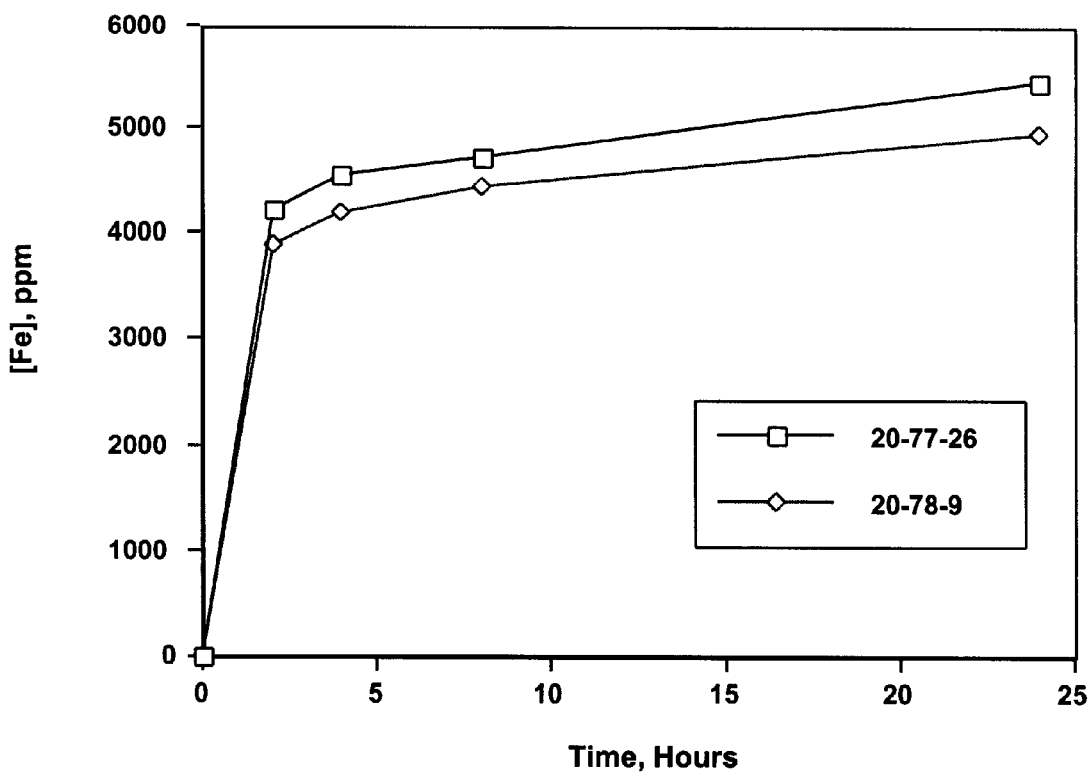
Figure 16:
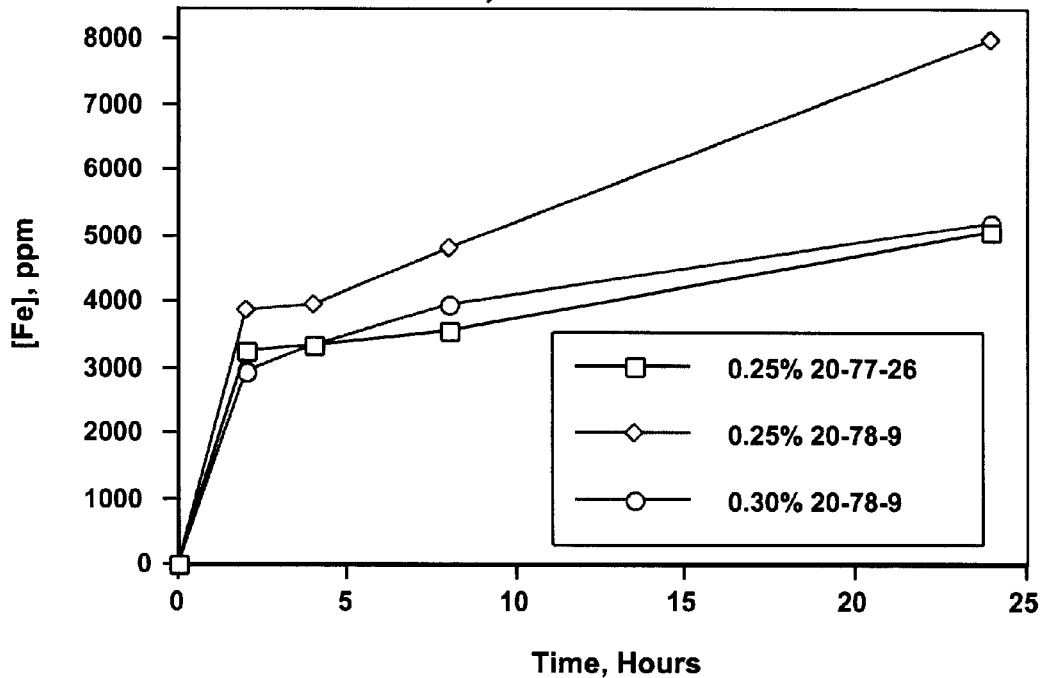
Figure 17:
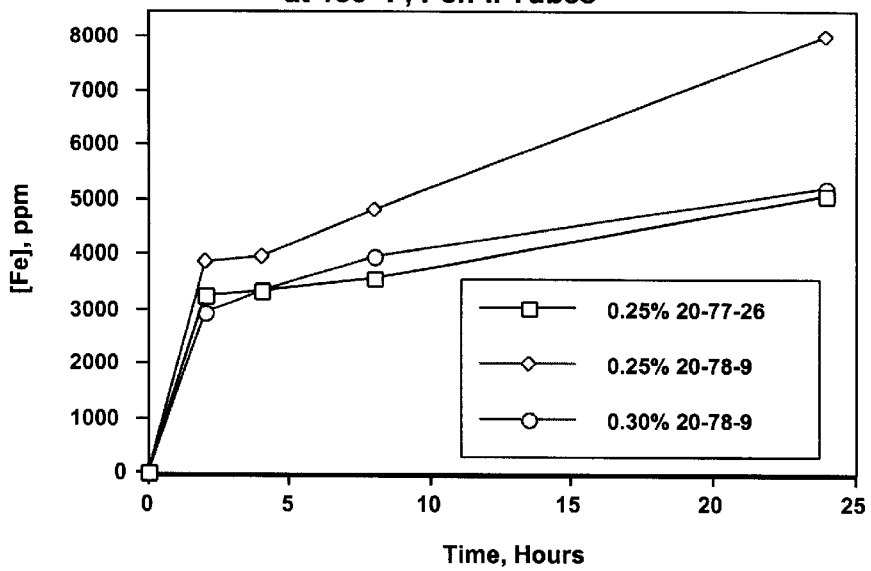

The results of the replicant at temperatures of 150° F., 130° F. and 110° F. are illustrated in FIGS. 11–13. All of the tested inhibitors allow the solvent to completely remove any plated copper in six hours at 150° F. At 130° F., at least 90% of the copper was removed. Even at 110° F., satisfactory copper removal was achieved with superior results being shown with the formulation using the mercaptoacetic acid.

Static corrosion rates for these formulations in the five solvents are summarized in the following table:

TABLE 8

Static Corrosion Rates

| Formulation | Sol A[1] lb/ft$^2$/day | Sol B[2] lb/ft$^2$/day | Sol C[2] lb/ft$^2$/day | Sol D[2] lb/ft$^2$/day | Sol E[3] lb/ft$^2$/day |
|---|---|---|---|---|---|
| A251 | 0.0014 | 0.0036 | 0.0025 | 0.0025 | 0.0014 |
| A224 | 0.0055 | 0.0031 | 0.0022 | 0.0022 | NA |
| 18-23-33 | 0.0013 | 0.0031 | 0.0020 | 0.0021 | 0.0012 |
| 20-16-35 | 0.0040 | 0.0030 | 0.0017 | 0.0025 | NA |
| 20-28-12 | 0.0025 |  | 0.0021 | 0.0021 | 0.0011 |

TABLE 8-continued

Static Corrosion Rates

| Formulation | Sol A[1] lb/ft²/day | Sol B[2] lb/ft²/day | Sol C[2] lb/ft²/day | Sol D[2] lb/ft²/day | Sol E[3] lb/ft²/day |
|---|---|---|---|---|---|
| 20-48-23 | 0.0024 | 0.0015 | 0.0030 | 0.0023 | 0.0015 |
| 20-65-4 | 0.0023 | 0.0010 | 0.0020 | 0.0026 | NA |

[1]1010 CS, 0.1% Inh, 300° F., s/v = 0.35 cm⁻¹
[2]1010 CS, 0.1% Inh, 200° F., s/v = 0.35 cm⁻¹
[3]1010 CS, 0.1% Inh, 150° F., s/v = 0.35 cm⁻¹

All of the inhibitor formulations tested provide superior static corrosion results.

In order to study the effect of different sulfur-containing compounds on the corrosion rate when used with inhibitor formulations in accord with the present invention, several test formulations were prepared. Test formulations using DDPB prepared in DPM and further including water, a surfactant (nonyl phenol with 15 EO) and one or more sulfur-containing compounds were prepared. Sulfur-containing compounds tested include diethyl thiourea, ammonium thiocyanate and mercaptoacetic acid. The composition of these formulations is summarized in Table 9.

TABLE 9

Test Formulations

| Formulation | DDPB/ DPM (%) | DPM (%) | Water (%) | Surfactant NP (15 EO) (%) | Sulfur Compounds (%) | Deodorant (%) | Flash Point (° F.) |
|---|---|---|---|---|---|---|---|
| 20-28-12 | 40 | 34 | 14 | 5 | diethyl thiourea-5 ammonium thiocyanate-2 | 0 | >200 |
| 20-48-23 | 39 | 34 | 16 | 5 | mercapto-acetic acid-6 | 0 | >200 |
| 20-77-26 | 40 | 24 | 24 | 5 | diethyl thiourea-5 ammonium thiocyanate-2 | 0 | >200 |
| 20-78-9 | 40 | 25 | 24 | 5 | mercapto-acetic acid-6 | 0 | >200 |
| 25-04-32 | 40 | 24 | 24 | 5 | mercapto-acetic acid-6 | 1 | >200 |

These formulations were employed in a series of static corrosion tests conducted in accord with the procedure described above. The results of these tests are reported in Tables 10 and 11.

TABLE 10

Static Corrosion Test with 0.2% 20-77-26 Inh.

| Metal | 10% Sol A 300° F. | 10% Sol B 200° F. | 3% Sol C 200° F. | 2% Sol D 200° F. | 10% Sol E 150° F. |
|---|---|---|---|---|---|
| 1018 CS | 0.0032 | 0.0044 | 0.0020 | 0.0020 | 0.0010 |
| SA-213-T11 | 0.0027 | 0.0034 | 0.0021 | 0.0018 | 0.0014 |
| SA-213-T22 | 0.0031 | 0.0037 | 0.0022 | 0.0020 | 0.0030 |
| SA-209T1a | 0.0028 | 0.0023 | 0.0019 | 0.0020 | 0.0090 |
| 515 Gr70 | 0.0020 | 0.0031 | 0.0020 | 0.0020 | 0.0099 | s/v 0.6 cm⁻¹; all corrosion rates are lb/ft²/day.

TABLE 11

Static Corrosion Test with 0.2% 20-78-9 Inh.

| Metal | 10% Sol A 300° F. | 10% Sol B 200° F. | 3% Sol C 200° F. | 2% Sol D 200° F. | 10% Sol E 150° F. |
|---|---|---|---|---|---|
| 1018 CS | 0.0022 | 0.0040 | 0.0018 | 0.0026 | 0.0010 |
| SA-213-T11 | 0.0010 | 0.0037 | 0.0036 | 0.0028 | 0.0015 |
| SA-213-T22 | 0.0020 | 0.0018 | 0.0032 | 0.0040 | 0.0025 |
| SA-209T1a | 0.0021 | 0.0040 | 0.0027 | 0.0030 | 0.0013 |
| 515 Gr70 | 0.0013 | 0.0038 | 0.0020 | 0.0022 | 0.0013 | s/v 0.6 cm⁻¹; all corrosion rates are lb/ft²/day.

The inhibitors tested provided satisfactory results in all of the solvents.

Because of the strong sulfur odor associated with mercaptoacetic acid, it may be desirable to employ a masking agent or deodorant to reduce the offensive odor. One exemplary agent is lemon oil.

Scale dissolution tests were conducted in accord with the procedure described above. Tests were conducted on the Pen-II tubes having a scale comprised mostly of magnetite, on the Georgia Power tubes with magnetite and copper scale and on the Hamilton tubes with heavy iron/copper scale.

The results of the tests on the Pen-II tubes are illustrated in FIGS. 14–17. The tested solutions cleaned 100% of the scale in less than 24 hours and provided adequate corrosion protection. However, because of higher than expected corrosion rates in Sol E, it was determined that the concentration of inhibitor should be increased to 0.3% in this solution.

Figure 18:
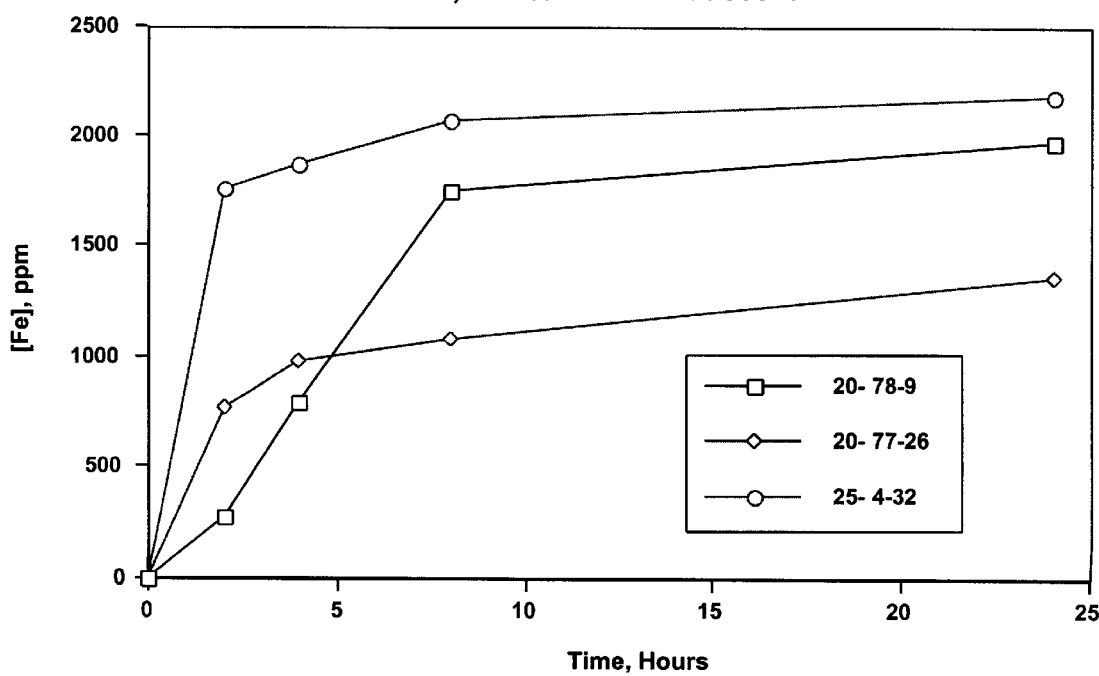
Figure 19:
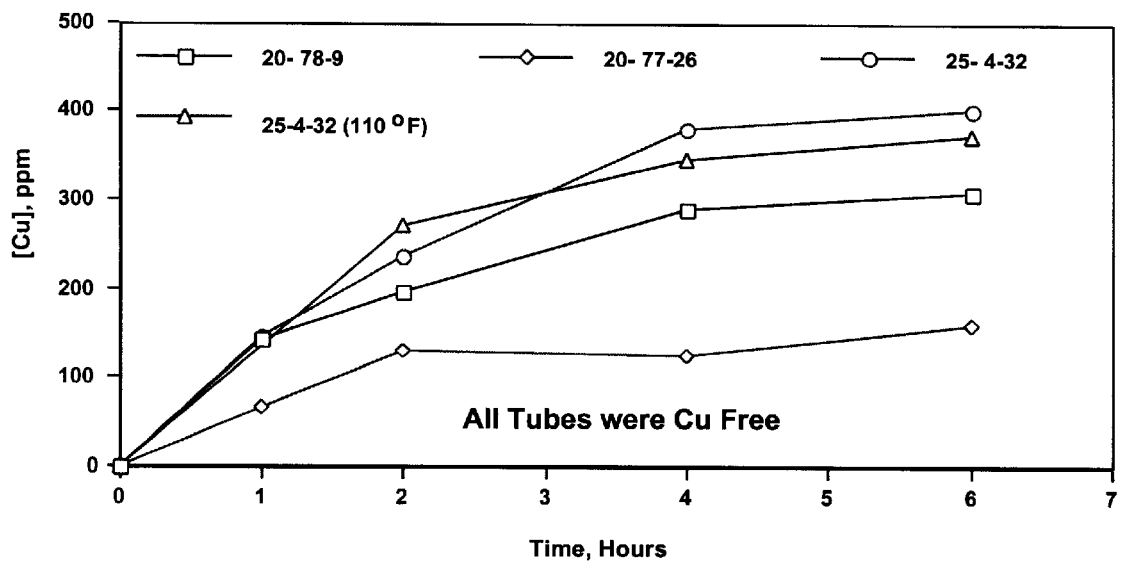
Figure 20:
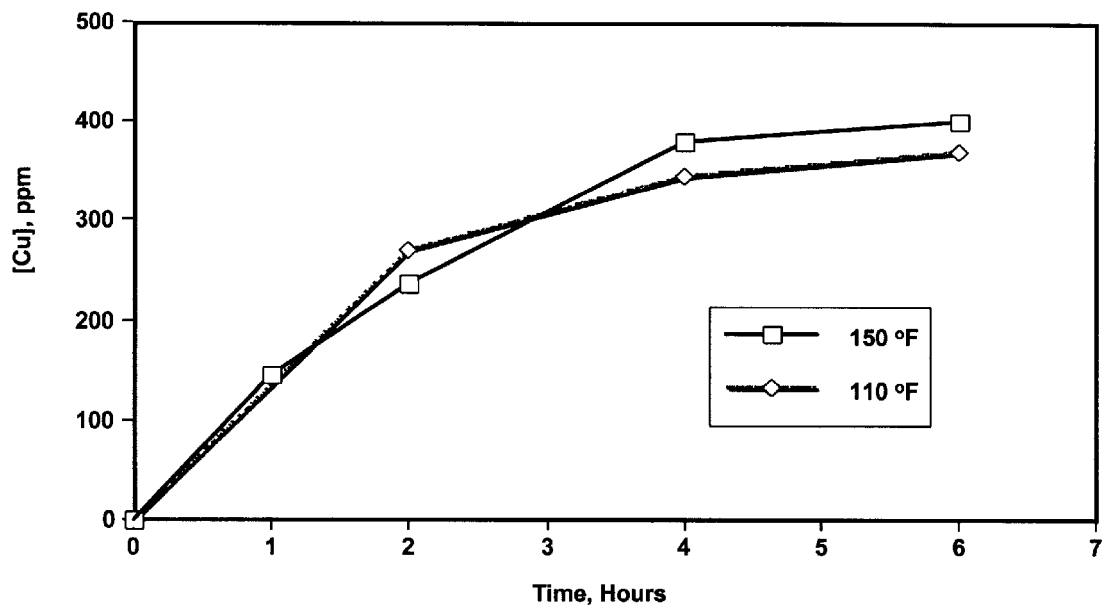

The Georgia Power tubes were fouled with both iron oxide and copper deposits. The previously described process for removing both iron oxide and copper was applied to these tubes. The results of the iron removal step are illustrated in FIG. 18. Using the iron solution generated in this step, copper removal was accomplished by lowering the temperature to 150° F. and injecting 30% hydrogen peroxide into the bomb. Copper removal results are illustrated in FIG. 19. There were no significant differences in the rate of copper removal. FIG. 20 compares the rate of copper removal at 150° F. with that at 110° F. While inhibitor 25-4-32 would permit copper removal at lower temperatures, all three tested inhibitors showed satisfactory results.

Shelf-life tests were conducted by exposing the inhibitor formulations to storage for 180 days at both room temperature and 110° F. At the conclusion of storage under these conditions, inhibitor solutions were used in static corrosion tests. The results of these tests are reported in Tables 12–17. No loss of inhibitor quality was seen.

TABLE 12

Static Corrosion Test with 0.2% 20-77-26 Inh.
120-Day Shelf Life Test

| Metal | Storage Temp ° F. | 10% Sol A 300° F. | 10% Sol B 200° F. | 3% Sol C 200° F. |
|---|---|---|---|---|
| 1018 CS | 72 | 0.0020 | 0.0036 | 0.0013 |
| 1018 CS | 110 | 0.0030 | 0.0030 | 0.0022 |
| SA-213-T11 | 72 | 0.0016 | 0.0027 | 0.0025 |
| SA-213-T11 | 110 | 0.0020 | 0.0012 | 0.0013 | s/v 0.6 cm$^{-1}$; all corrosion rates are lb/ft$^2$/day.

TABLE 13

Static Corrosion Tests with 0.2% 20-78-9 Inh.
120-Day Shelf Life Test

| Metal | Storage Temp ° F. | 10% Sol A 300° F. | 10% Sol B 200° F. | 3% Sol C 200° F. |
|---|---|---|---|---|
| 1018 CS | 72 | 0.0020 | 0.0030 | 0.0020 |
| 1018 CS | 110 | 0.0020 | 0.0035 | 0.0017 |
| SA-213-T11 | 72 | 0.0015 | 0.0015 | 0.0018 |
| SA-213-T11 | 110 | 0.0015 | 0.0028 | 0.0031 | s/v 0.6 cm$^{-1}$; all corrosion rates are lb/ft$^2$/day.

TABLE 14

Static Corrosion Tests with 0.2% 20-78-9 Inh.
120-Day Shelf Life Test

| Metal | Storage Temp ° F. | 10% Sol A 300° F. | 10% Sol B 200° F. | 3% Sol C 200° F. |
|---|---|---|---|---|
| 1018 CS | 72 | 0.0026 | 0.0020 | 0.0018 |
| 1018 CS | 110 | 0.0018 | 0.0025 | 0.0021 |
| SA-213-T11 | 72 | 0.0020 | 0.0017 | 0.0022 |
| SA-213-T11 | 110 | 0.0014 | 0.0010 | 0.0024 | s/v 0.6 cm$^{-1}$; all corrosion rates are lb/ft$^2$/day.

TABLE 15

Static Corrosion Tests with 0.2% 20-77-26 Inh.
120-Day Shelf Life Test

| Metal | Storage Temp ° F. | 10% Sol A 300° F. | 10% Sol B 200° F. | 3% Sol C 200° F. |
|---|---|---|---|---|
| 1018 CS | 72 | 0.0028 | 0.0038 | 0.0017 |
| 1018 CS | 110 | 0.0026 | 0.0035 | 0.0017 |
| SA-213-T11 | 72 | 0.0012 | 0.0010 | 0.0015 |
| SA-213-T11 | 110 | 0.0018 | 0.0020 | 0.0015 | s/v 0.6 cm$^{-1}$; all corrosion rates are lb/ft$^2$/day.

TABLE 16

Static Corrosion Tests with 0.2% 20-78-9 Inh.
120-Day Shelf Life Test

| Metal | Storage Temp ° F. | 10% Sol A 300° F. | 10% Sol B 200° F. | 3% Sol C 200° F. |
|---|---|---|---|---|
| 1018 CS | 72 | 0.0030 | 0.0039 | 0.0018 |
| 1018 CS | 110 | 0.0018 | 0.0040 | 0.0016 |

TABLE 16-continued

Static Corrosion Tests with 0.2% 20-78-9 Inh.
120-Day Shelf Life Test

| Metal | Storage Temp ° F. | 10% Sol A 300° F. | 10% Sol B 200° F. | 3% Sol C 200° F. |
|---|---|---|---|---|
| SA-213-T11 | 72 | 0.0011 | 0.0010 | 0.0023 |
| SA-213-T11 | 110 | 0.0010 | 0.0024 | 0.0026 | s/v 0.6 cm$^{-1}$; all corrosion rates are lb/ft$^2$/day.

TABLE 17

Static Corrosion Tests with 0.2% 25-4-32 Inh.
120-Day Shelf Life Test

| Metal | Storage Temp ° F. | 10% Sol A 300° F. | 10% Sol B 200° F. | 3% Sol C 200° F. |
|---|---|---|---|---|
| 1018 CS | 72 | 0.0020 | 0.0040 | 0.0016 |
| 1018 CS | 110 | 0.0020 | 0.0038 | 0.0020 |
| SA-213-T11 | 72 | 0.0016 | 0.0010 | 0.0026 |
| SA-213-T11 | 110 | 0.0018 | 0.0010 | 0.0029 | s/v 0.6 cm$^{-1}$; all corrosion rates are lb/ft$^2$/day.

Figure 21:
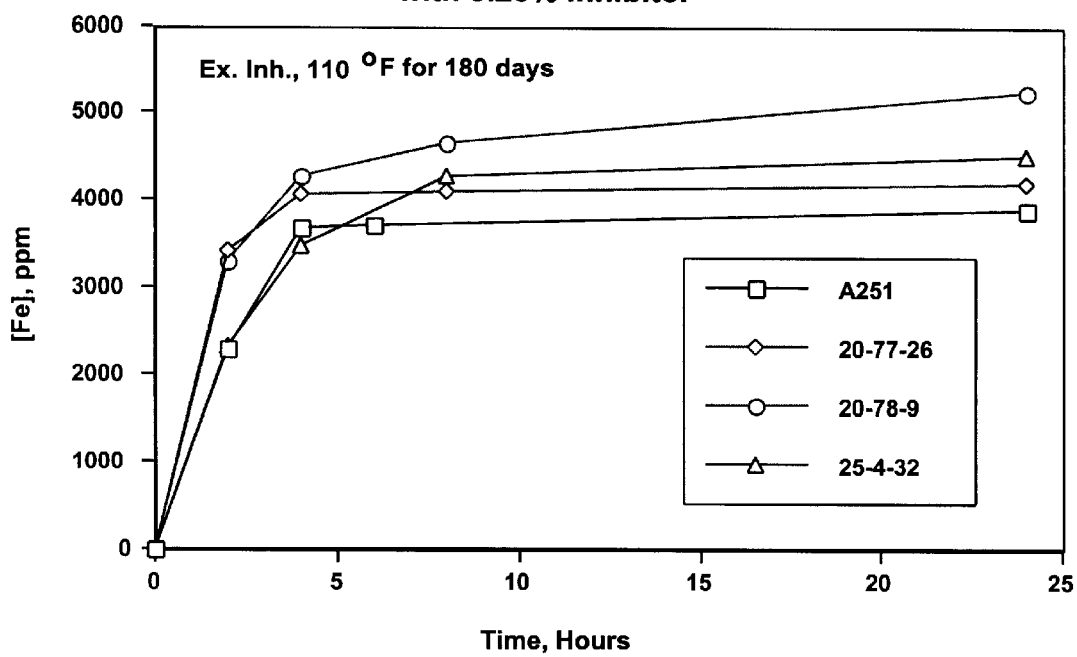
Figure 22:
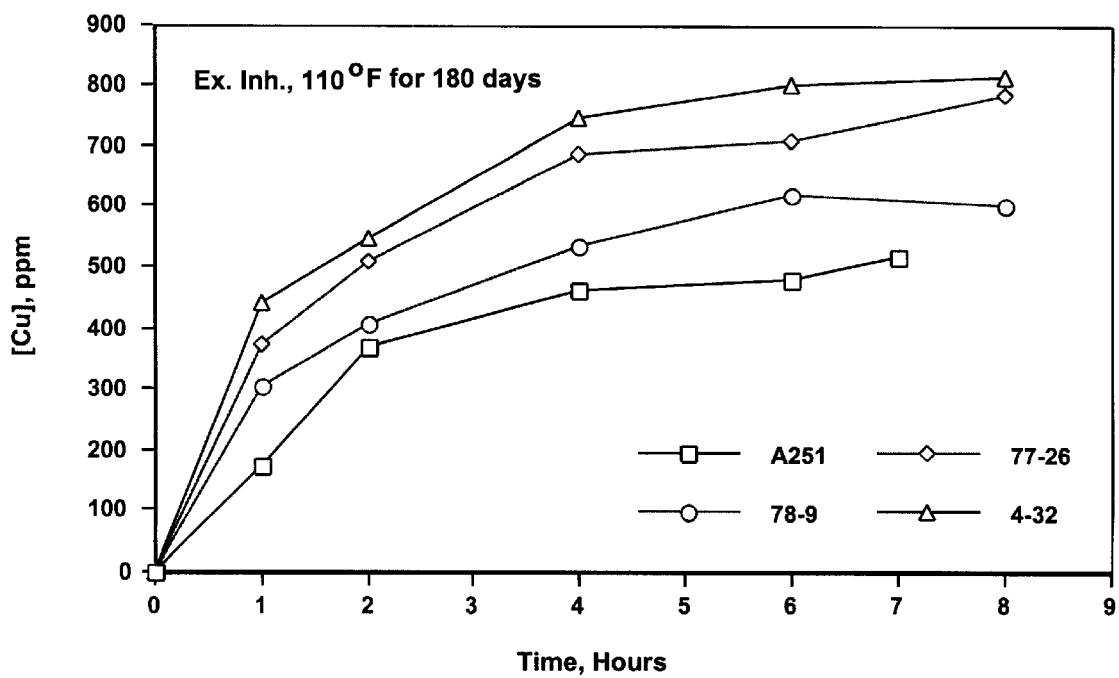

In order to test the stored corrosion inhibitors of the present invention with scale including high copper content, boiler tube samples from a unit in the city of Hamilton, Ohio, were tested. The scale on these tubes contained 24% copper. These tubes were cleaned to remove iron oxide and copper. Iron dissolution and copper removal curves are shown in FIGS. 21 and 22. Satisfactory results were observed.

Figure 23:
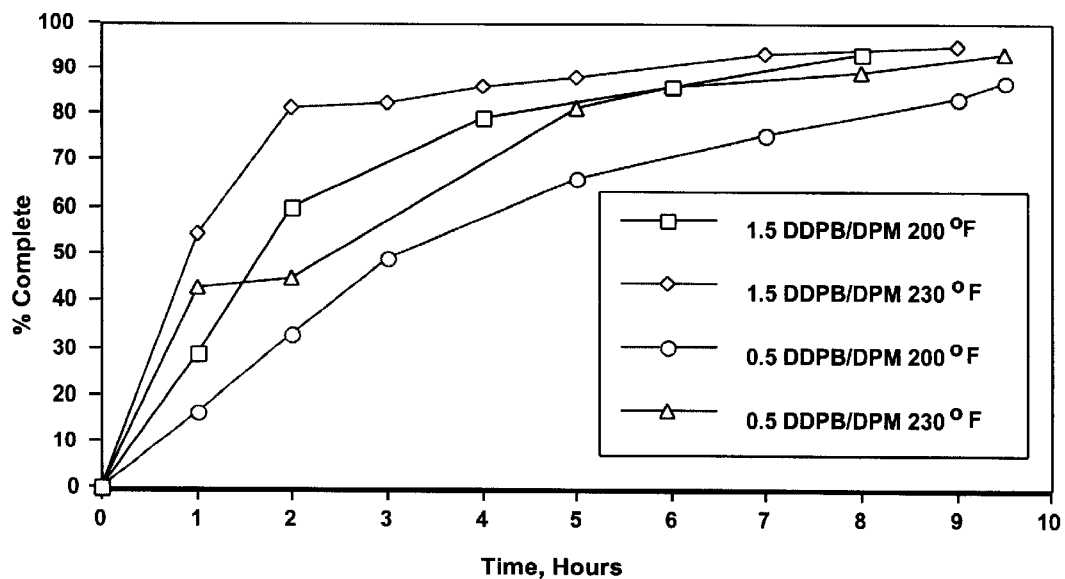

The effect of the ratio of DDPB to DPM in the quaternary ammonium salt preparation was examined by varying the weight ratio of DDPB to DPM from 0.5:1 to 1.5:1. The effect of temperature on the reaction rate was also examined at 200° F. and 230° F. The results of these tests are illustrated in FIG. 23. From these tests it appears that it is preferable to conduct the reaction at the higher temperature and weight ratio of quaternary salt to solvent.

Figure 24:
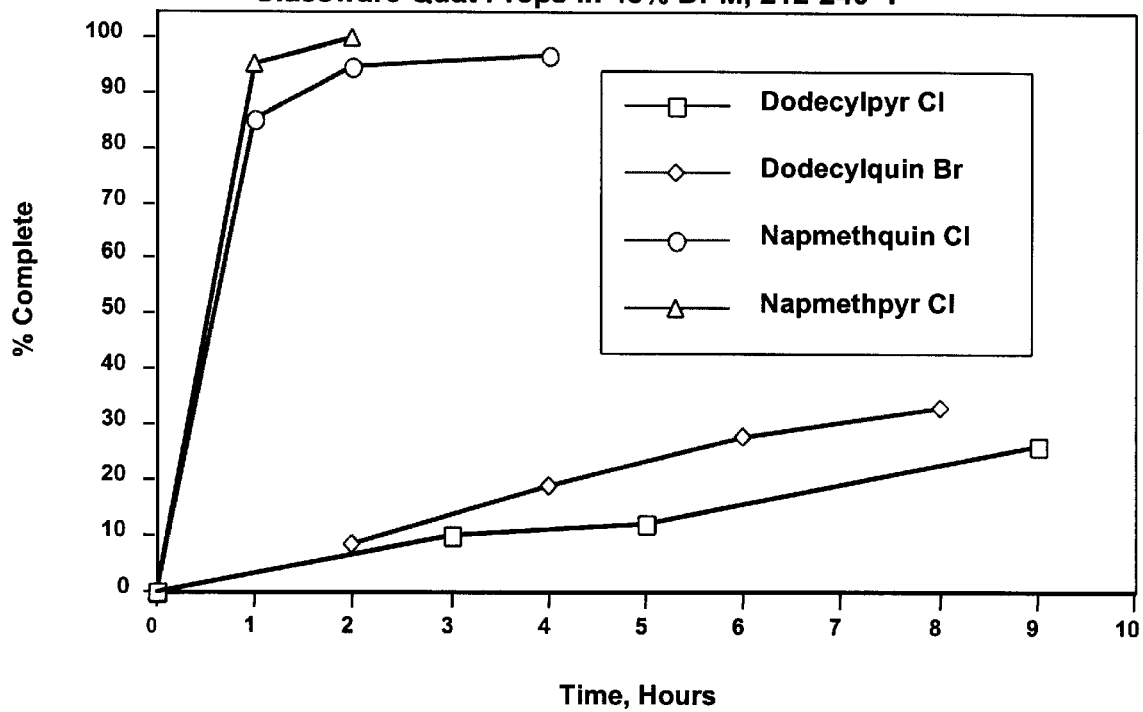

While DDPB is the preferred quaternary ammonium salt, four alternate salts were prepared. In two preparations, chloro methyl naphthalene was reacted with, respectively, quinoline and pyridine. In another preparation, dodecyl bromide was reacted with quinoline. In the final preparation, dodecyl chloride was reacted with pyridine. The rates observed in these reactions are illustrated in FIG. 24. The results of these tests show that bromide is a better leaving group than chloride and that a halide bonded to a carbon atom conjugated to an aromatic ring appears to be a better leaving group than a halide attached to carbon next to another aliphatic carbon. These examples confirm that pyridine is a better nucleophile than quinoline in this reaction.

Field Test

In order to confirm the successful performance of the corrosion inhibitors of the present invention in an actual industrial setting, a pilot plant preparation and field test was arranged. Initially, a quantity of dodecyl pyridinium bromide (DDPB) was prepared in accord with the present invention using dipropylene glycol methyl ether (DPM) as the solvent. A reaction vessel containing 268 lb DPM, 87 lb pyridine and 137 lb dodecyl bromide was heated to about 185° F. to initiate the reaction. After about 1 hour at temperature, an additional 136 lb dodecyl bromide was added and the temperature raised to about 230° F. The vessel was sampled hourly and the progress of the reaction followed by monitoring the bromide concentration using a silver nitrate autotitrator. After 4 hours at temperature, 47 lb water was added. After 6 hours, the temperature was raised to 240° F. At 7.5 hours, the reactor was cooled below 150° F., 402 lb of DPM was added. The mixture then was allowed to stand for about 16 hours.

Figure 25:
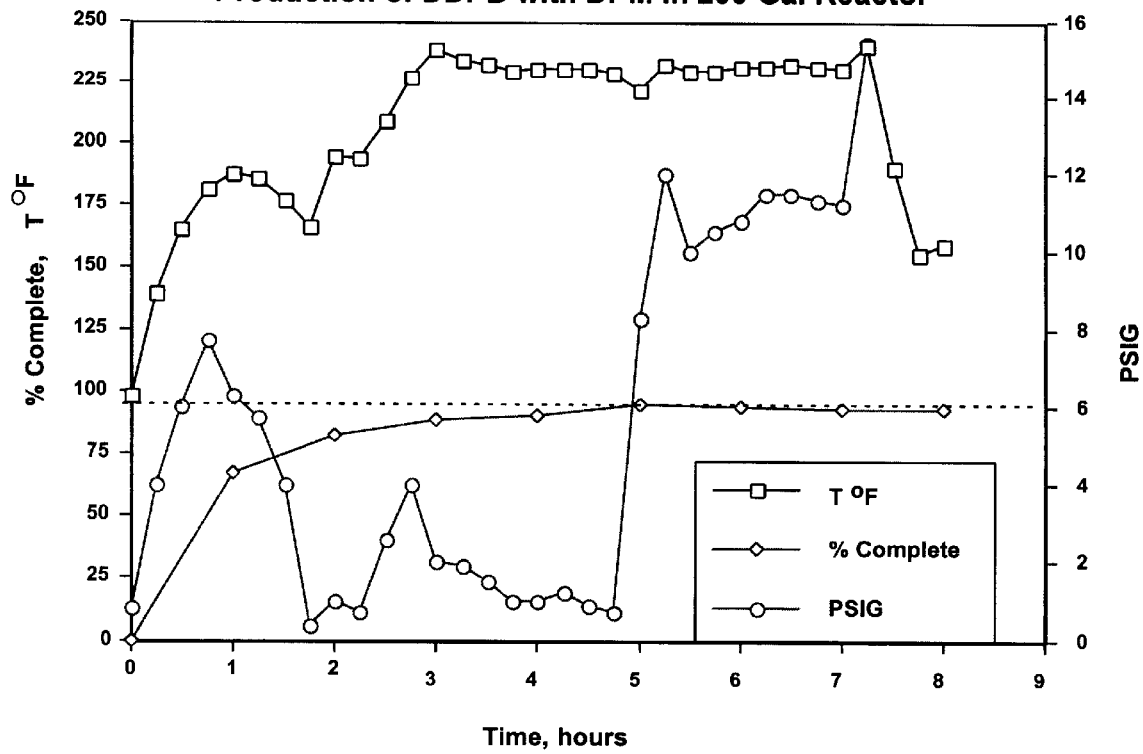

The reaction coordinate, temperatures and pressures measured during this preparation are illustrated in FIG. 25. The loss of temperature after 1 hour was due to the injection of the second portion of DPM. The reaction appeared to be complete after 5 hours following injection of water at the 4-hour mark. The reaction was terminated at 7.5 hours by addition of the remainder of the DPM. The initial pressure in the reactor was probably due to unreacted pyridine. While the DDB was added in two batches in this preparation, it may all be added initially, if desired.

A corrosion inhibitor composition was prepared from the foregoing mixture by adding 430 lb water, 84 lb nonionic surfactant (nonyl phenol with 15 EO) and 100 lb mercaptoacetic acid with stirring at 100° F. If desired, a deodorant such as lemon oil may be included. In this instance, 16 lb of lemon oil was added. The pH of the final solution was about 1.8. The pH may be increased, if desired, e.g., by addition of 0.1% monoethanolamine (MEA).

A series of static corrosion tests were conducted in accord with the previously described procedure using 24-hour tests at s/v ratios of 0.6 cm$^{-1}$ and 1.0 cm$^{-1}$. The test results are reported in Tables 18–25. In general, an inhibitor loading of 0.2% was satisfactory for all metals and all s/v ratios.

TABLE 18

Static Corrosion Rates for Field Test Inhibitor in Sol A at 300° F.

| Conc. Sol A (%) | s/v, cm$^{-1}$ | Inhibitor (%) | Metal | Rate lb/ft$^2$/day |
|---|---|---|---|---|
| 10 | 0.6 | 0.1 | AISI 1018 | 0.0013 |
| 10 | 0.6 | 0.2 | AISI 1018 | 0.0014 |
| 10 | 0.6 | 0.1 | SA 515 gr 70 | 0.0010 |
| 10 | 0.6 | 0.2 | SA 515 gr 70 | 0.0011 |
| 10 | 0.6 | 0.2 | SA 209T1a | 0.0010 |
| 10 | 0.6 | 0.2 | SA 213T11 | 0.0014 |
| 10 | 0.6 | 0.2 | SA 213T22 | 0.0020 |
| 10 | 1.0 | 0.2 | AISI 1018 | 0.0011 |
| 10 | 1.0 | 0.2 | SA 515 gr 70 | 0.0011 |
| 10 | 1.0 | 0.2 | SA 209T1a | 0.0013 |
| 10 | 1.0 | 0.2 | SA 213T11 | 0.0013 |
| 10 | 1.0 | 0.3 | SA 213T11 | 0.0011 |
| 10 | 1.0 | 0.2 | SA 213T22 | 0.0016 |
| 10 | 1.0 | 0.3 | SA 213T22 | 0.0014 |
| 20 | 1.0 | 0.2 | SA 515 gr 70 | 0.0010 |
| 20 | 1.0 | 0.2 | SA 209T1a | 0.0053 |
| 20 | 1.0 | 0.2 | SA 213T22 | 0.0031 |

TABLE 19

Static Corrosion Rates for Field Test Inhibitor in Sol B at 200° F.

| Conc. Sol B (%) | s/v, cm$^{-1}$ | Inhibitor (%) | Metal | Rate lb/ft$^2$/day |
|---|---|---|---|---|
| 10 | 0.6 | 0.1 | AISI 1018 | 0.0022 |
| 10 | 0.6 | 0.2 | AISI 1018 | 0.0021 |
| 10 | 0.6 | 0.1 | SA 515 gr 70 | 0.0020 |
| 10 | 0.6 | 0.2 | SA 515 gr 70 | 0.0021 |
| 10 | 0.6 | 0.2 | SA 209T1a | 0.0010 |
| 10 | 0.6 | 0.2 | SA 213T11 | 0.0021 |
| 10 | 0.6 | 0.2 | SA 213T22 | 0.0010 |
| 10 | 1.0 | 0.2 | AISI 1018 | 0.0020 |
| 10 | 1.0 | 0.2 | SA 515 gr 70 | 0.0019 |
| 10 | 1.0 | 0.2 | SA 209T1a | 0.0010 |
| 10 | 1.0 | 0.2 | SA 213T11 | 0.0020 |

TABLE 19-continued

Static Corrosion Rates for Field Test Inhibitor in Sol B at 200° F.

| Conc. Sol B (%) | s/v, cm$^{-1}$ | Inhibitor (%) | Metal | Rate lb/ft$^2$/day |
|---|---|---|---|---|
| 10 | 1.0 | 0.2 | SA 213T22 | 0.0010 |
| 10 | 1.0 | 0.3 | SA 213T11 | 0.0019 |
| 10 | 1.0 | 0.3 | SA 213T22 | 0.0010 |
| 20 | 1.0 | 0.2 | SA 515 gr 70 | 0.0014 |
| 20 | 1.0 | 0.2 | SA 209T1a | 0.0010 |
| 20 | 1.0 | 0.2 | SA 213T22 | 0.0010 |

TABLE 20

Static Corrosion Rates for Field Test Inhibitor in Sol C at 200° F.

| Conc. Sol C (%) | s/v, cm$^{-1}$ | Inhibitor (%) | Metal | Rate lb/ft$^2$/day |
|---|---|---|---|---|
| 3 | 1.0 | 0.2 | AISI 1018 | 0.0015 |
| 3 | 1.0 | 0.2 | SA 515 gr 70 | 0.0014 |
| 3 | 1.0 | 0.2 | SA 209T1a | 0.0027 |
| 3 | 1.0 | 0.2 | SA 213T11 | 0.0024 |
| 3 | 1.0 | 0.2 | SA 213T22 | 0.0030 |
| 6 | 1.0 | 0.2 | AISI 1018 | 0.0012 |
| 6 | 1.0 | 0.2 | SA 515 gr 70 | 0.0015 |
| 6 | 1.0 | 0.2 | SA 209T1a | 0.0045 |
| 6 | 1.0 | 0.2 | SA 213T11 | 0.0027* |
| 6 | 1.0 | 0.2 | SA 213T22 | 0.0039* |
| 3/0.25% Y1 | 1.0 | 0.2 | SA 213T11 | 0.0026* |
| 3/0.25% Y1 | 1.0 | 0.2 | SA 213T22 | 0.0026* |

*Very slight pit

TABLE 21

Static Corrosion Rates for Field Test Inhibitor in Sol D at 200° F.

| Conc. Sol D (%) | s/v, cm$^{-1}$ | Inhibitor (%) | Metal | Rate lb/ft$^2$/day |
|---|---|---|---|---|
| 2 | 1.0 | 0.2 | AISI 1018 | 0.0020 |
| 2 | 1.0 | 0.2 | SA 515 gr 70 | 0.0014 |
| 2 | 1.0 | 0.2 | SA 209T1a | 0.0026 |
| 2 | 1.0 | 0.2 | SA 213T11 | 0.0022 |
| 2 | 1.0 | 0.2 | SA 213T22 | 0.0033 |
| 4 | 1.0 | 0.2 | AISI 1018 | 0.0022 |
| 4 | 1.0 | 0.2 | SA 515 gr 70 | 0.0019 |
| 4 | 1.0 | 0.2 | SA 209T1a | 0.0038 |
| 4 | 1.0 | 0.2 | SA 213T11 | 0.0028 |
| 4 | 1.0 | 0.2 | SA 213T22 | 0.012** |
| 4 | 1.0 | 0.3 | SA 213T22 | 0.0028 |
| 4/0.25% Y1 | 1.0 | 0.2 | SA 213T11 | 0.0028 |
| 4/0.25% Y1 | 1.0 | 0.2 | SA 213T22 | 0.0030* |

*Very slight pit
**Deep pits

TABLE 22

Static Corrosion Rates for Field Test Inhibitor in Sol E at 150° F.

| Conc. Sol E (%) | s/v, cm$^{-1}$ | Inhibitor (%) | Metal | Rate lb/ft$^2$/day |
|---|---|---|---|---|
| 10 | 0.6 | 0.1 | AISI 1018 | 0.0015 |
| 10 | 0.6 | 0.2 | AISI 1018 | 0.0014 |
| 10 | 0.6 | 0.1 | SA 515 gr 70 | 0.0019 |
| 10 | 0.6 | 0.2 | SA 515 gr 70 | 0.0014 |
| 10 | 0.6 | 0.2 | SA 209T1a | 0.0033 |
| 10 | 0.6 | 0.2 | SA 213T11 | 0.0037 |
| 10 | 0.6 | 0.2 | SA 213T22 | 0.0034 |
| 10 | 1.0 | 0.2 | AISI 1018 | 0.0013 |
| 10 | 1.0 | 0.2 | SA 515 gr 70 | 0.0013 |

TABLE 22-continued

Static Corrosion Rates for Field Test Inhibitor in Sol E at 150° F.

| Conc. Sol E (%) | s/v, $cm^{-1}$ | Inhibitor (%) | Metal | Rate lb/$ft^2$/day |
|---|---|---|---|---|
| 10 | 1.0 | 0.2 | SA 209T1a | 0.0029 |
| 10 | 1.0 | 0.2 | SA 213T11 | 0.0032 |
| 10 | 1.0 | 0.2 | SA 213T22 | 0.0025 |

TABLE 23

Static Corrosion Rates for Field Test Inhibitor in Ammonium Citrate, pH 3.5 at 200° F.

| Conc. Citrate (%) | s/v, $cm^{-1}$ | Inhibitor (%) | Metal | Rate lb/$ft^2$/day |
|---|---|---|---|---|
| 3 | 0.6 | 0.1 | AISI 1018 | 0.0024 |
| 3 | 0.6 | 0.2 | AISI 1018 | 0.0017 |
| 3 | 0.6 | 0.1 | SA 515 gr 70 | 0.0017 |
| 3 | 0.6 | 0.2 | SA 515 gr 70 | 0.0020 |
| 3 | 0.6 | 0.2 | SA 209T1a | 0.0031 |
| 3 | 0.6 | 0.2 | SA 213T11 | 0.0011 |
| 3 | 0.6 | 0.2 | SA 213T22 | 0.0019 |
| 3 | 1.0 | 0.2 | AISI 1018 | 0.0014 |
| 3 | 1.0 | 0.2 | SA 515 gr 70 | 0.0015 |
| 3 | 1.0 | 0.2 | SA 209T1a | 0.0025 |
| 3 | 1.0 | 0.2 | SA 213T11 | 0.0011 |
| 3 | 1.0 | 0.2 | SA 213T22 | 0.0015 |

TABLE 24

Static Corrosion Rates for Field Test Inhibitor in Ammonium Citrate, pH 6.5 at 300° F.

| Conc. Citrate (%) | s/v, $cm^{-1}$ | Inhibitor (%) | Metal | Rate lb/$ft^2$/day |
|---|---|---|---|---|
| 3 | 0.6 | 0.2 | AISI 1018 | 0.0018 |
| 3 | 0.6 | 0.2 | SA 515 gr 70 | 0.0018 |
| 3 | 0.6 | 0.2 | SA 209T1a | 0.0015 |
| 3 | 0.6 | 0.2 | SA 213T11 | 0.0021 |
| 3 | 0.6 | 0.2 | SA 213T22 | 0.0027 |
| 3 | 1.0 | 0.2 | AISI 1018 | 0.0019 |
| 3 | 1.0 | 0.2 | SA 515 gr 70 | 0.0013 |
| 3 | 1.0 | 0.2 | SA 209T1a | 0.0018 |
| 3 | 1.0 | 0.2 | SA 213T11 | 0.0021 |
| 3 | 1.0 | 0.2 | SA 213T22 | 0.0034 |

TABLE 25

Static Corrosion Rates for Field Test Inhibitor in Misc. Solvents at 150° F.

| Conc., Acid (%) | s/v, $cm^{-1}$ | Inhibitor (%) | Metal | Rate lb/$ft^2$/day |
|---|---|---|---|---|
| 10% Sulfuric | 0.6 | 0.2 | AISI 1018 | 0.0015 |
| 10% Sulfuric | 0.6 | 0.2 | SA 515 gr 70 | 0.0025 |
| 15% Sulfuric | 0.6 | 0.2 | AISI 1018 | 0.0017 |
| 15% Sulfuric | 0.6 | 0.2 | SA 515 gr 70 | 0.0043 |
| 7.5% HSSR* | 0.6 | 0.2 | AISI 1018 | 0.0010 |
| 7.5% HSSR | 0.6 | 0.2 | SA 515 gr 70 | 0.0018 |
| 15% HSSR | 0.6 | 0.2 | AISI 1018 | 0.0069 |
| 15% HSSR | 0.6 | 0.2 | SA 515 gr 70 | 0.0058 |
| 7.5% HSSR | 0.6 | 0.3 | 410 | 0.0180 |
| 10% Sulfamic | 0.6 | 0.2 | AISI 1018 | 0.0013 |
| 10% Sulfamic | 0.6 | 0.2 | SA 515 gr 70 | 0.0010 |
| 20% Sulfamic | 0.6 | 0.2 | AISI 1018 | 0.0010 |
| 20% Sulfamic | 0.6 | 0.2 | SA 515 gr 70 | 0.0015 |

*HSSR is a sulfuric/glyoxal disclosed in U.S. Pat. No. 4,220,550.

Dynamic tests showed similar but also slightly higher corrosion rates. Accordingly, it is recommended that the inhibitor concentration be increased to 0.4%.

A corrosion inhibitor prepared in accord with the foregoing pilot plant example was used to clean a Babock & Wilcox natural circulation boiler and economizer with a nominal capacity of about 22,000 gallons. Tube analyses performed before cleaning showed an even deposit of about 16 g/$ft^2$ containing a mixture of iron, copper and nickel. Cleaning was undertaken using 3,000 gallons of 40% tetraammonium EDTA at a pH of about 9.2 (ChelClean™ 675) to which 35 gallons of the test inhibitor was added. This solution contained about 0.15% by volume inhibitor. After chemical injection, the unit was circulated by alternate firing to about 320° F. and cooling to about 250° F. An electric pump circulated the economizer.

Figure 26:
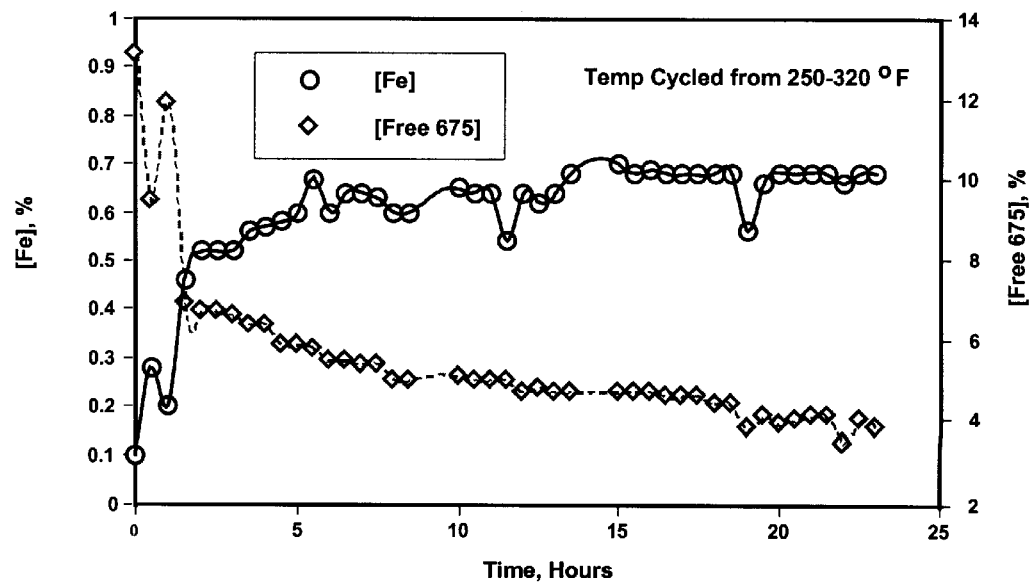

The concentrations of iron and free EDTA in the ChelClean™ 675 cleaning solution stabilized after about 10 hours. These concentrations remained substantially constant for the following 12 hours. The unit was cooled to 150° F. These concentrations are reported in FIG. 26.

Figure 27:
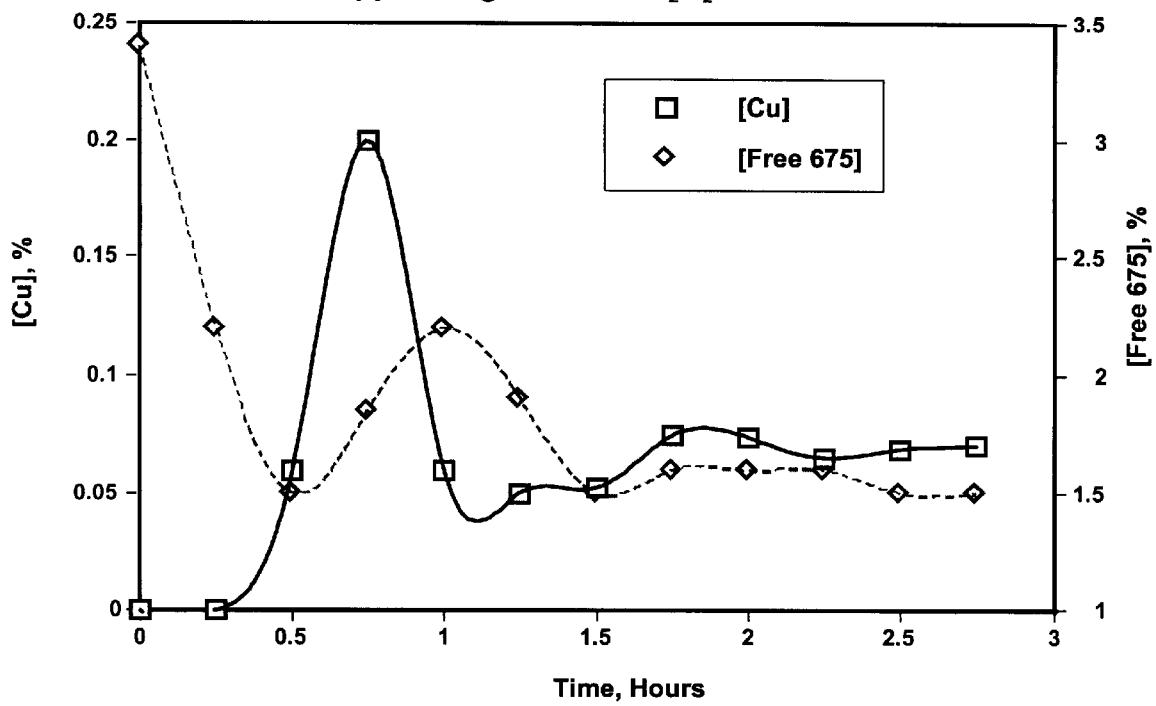
Figure 28:
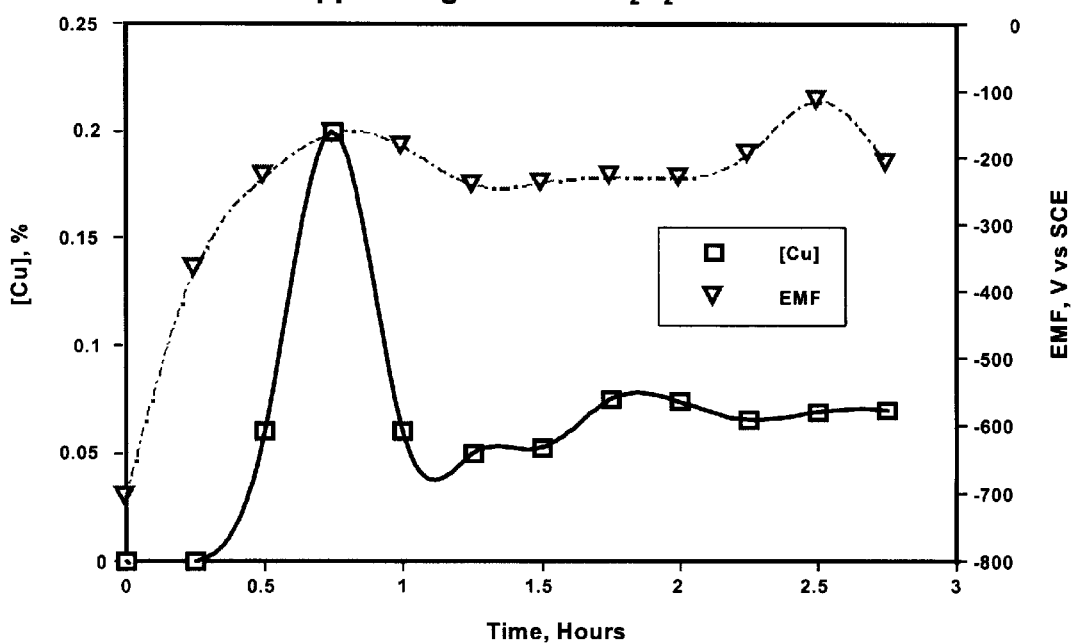

Air and 30% hydrogen peroxide were injected through two different ports on the lower headers. After initial rapid changes, the copper and free EDTA concentrations leveled off at about 2 hours. The EMF readings, reflecting the change in the ratio of ferrous to ferric iron, also changed rapidly. These values are recorded in FIGS. 27 and 28.

The cleaning was terminated after 3 hours of oxidation with stable copper and free EDTA concentrations. Following termination of cleaning, the equipment was drained and rinsed. The treated solution was analyzed, and it was determined that the quantity of metals removed closely corresponded to the amounts predicted from the preliminary scale analyses. It was determined that the inhibitor had performed satisfactorily and provided adequate protection to the unit without interference with copper removal.

The foregoing description of the invention has been directed in primary part to particular preferred embodiments in accordance with the requirements of the Patent Statute and for purposes of explanation and illustration. It will be apparent, however, to those skilled in the art that many modifications and changes in the specifically described methods and compositions may be made without departing from the true scope and spirit of the invention. Therefore, the invention is not restricted to the preferred embodiments described and illustrated but covers all modifications that may fall within the scope of the following claims.

What is claimed is:

1. A method for preparing a pyridinium salt, comprising:
    contacting pyridine with dodecyl bromide in dipropylene glycol methyl ether as a solvent at a temperature above about 65° C.

2. A method for preparing a quaternary ammonium salt, comprising:
    contacting a tertiary ammonium compound selected from the group consisting of pyridine, substituted pyridines, quinoline, substituted quinolines and mixtures thereof with a second compound having the formula RX where R is aliphatic, substituted aliphatic or alkyl aryl and X is a monovalent anion;

said contacting proceeding in a solvent selected from the group consisting of propylene glycols, propylene glycol ethers and mixtures thereof, said solvent having a flash point greater than about 150° F.

3. The method of claim 2 wherein X is a halide and R is selected from the group consisting of alkyl and alkyl aryl moieties having from about 6 to about 18 carbon atoms.

4. The method of claim 3 wherein said tertiary ammonium compound is selected from the group consisting of pyridine, alkyl pyridine, quinoline, alkyl quinoline and mixtures thereof and R is selected from the group consisting of benzyl, naphthyl and alkyl moieties having from about 7 to about 16 carbon atoms.

5. The method of claim 2 wherein said tertiary ammonium compound is represented by the formula:

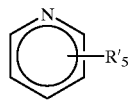

wherein each $R'_5$ independently is —H, —OH, —OR, —OROH, alkyl, alkenyl, alkynyl or halo.

6. The method of claim 2 wherein said tertiary ammonium compound is selected from the group consisting of pyridine, quinoline and mixtures thereof and said second compound is selected from the group consisting of alkyl bromides, alkyl aryl chlorides and mixtures thereof.

7. The method of claim 2 wherein said solvent is dipropylene glycol methyl ether.

8. The method of claim 2 wherein said tertiary ammonium compound is pyridine and said second compound is dodecyl bromide.

9. The method of claim 2 wherein said contacting proceeds at a temperature greater than about 65° C.

10. The method of claim 9 wherein said contacting proceeds at a temperature from about 75° to about 125° C.

11. The method of claim 2 further comprising the step of adding water during said contacting.

12. The method of claim 2 wherein the molar ratio of said tertiary ammonium compound to said second compound is about 1:1.

13. A method for preparing a quaternary ammonium salt, comprising:

forming a reaction mixture comprising,
a solvent selected from the group consisting of propylene glycols, propylene glycol ethers and mixtures thereof, said solvent having a flash point greater than about 150° F.;
a tertiary ammonium compound selected from the group consisting of pyridine, substituted pyridines, quinoline, substituted quinolines and mixtures thereof; and
an organic halide having the formula RX where R is aliphatic, substituted aliphatic or alkyl aryl and X is a halide; and heating said reaction mixture to a temperature greater than about 65° C. for a time sufficient for said tertiary ammonium compound and said organic halide to react.

14. The method of claim 13 wherein the molar ratio of said tertiary ammonium compound to said organic halide is about 1:1.

15. The method of claim 13 further comprising adding water to said reaction mixture.

16. The method of claim 13 wherein said tertiary ammonium compound is selected from the group consisting of pyridine, alkyl pyridine, quinoline, alkyl quinoline and mixtures thereof and R is selected from the group consisting of benzyl, naphthyl and akyl moieties having about 7–16 carbon atoms.

17. The method of claim 16 wherein said tertiary ammonium compound is selected from the group consisting of pyridine, quinoline and mixtures thereof and said organic halide is selected from the group consisting of alkyl bromides, alkyl aryl chlorides and mixtures thereof.

18. The method of claim 17 wherein said solvent is dipropylene glycol methyl ether.

19. The method of claim 18 wherein the molar ratio of said tertiary ammonium compound and said organic halide is about 1:1.

20. The method of claim 19 wherein said temperature is about 75–125° C.

* * * * *